United States Patent [19]

Young et al.

[11] Patent Number: 5,143,081
[45] Date of Patent: Sep. 1, 1992

[54] RANDOMIZED DOUBLE PULSE STIMULUS AND PAIRED EVENT ANALYSIS

[75] Inventors: Wise Young; Kaoru Sakatani, both of New York, N.Y.

[73] Assignee: New York University, New York, N.Y.

[21] Appl. No.: 558,345

[22] Filed: Jul. 27, 1990

[51] Int. Cl.$^5$ ............................................. A61B 5/00
[52] U.S. Cl. .................................... 128/741; 128/745; 128/746; 73/579
[58] Field of Search ............... 128/731, 732, 733, 741, 128/742, 745, 746; 73/579, 602, 659, 664

[56] References Cited

U.S. PATENT DOCUMENTS

| | | | |
|---|---|---|---|
| 3,780,724 | 12/1973 | John | 128/731 |
| 4,462,411 | 7/1984 | Richards | 128/731 |
| 4,763,666 | 8/1988 | Strian et al. | 128/742 |

Primary Examiner—Kyle L. Howell
Assistant Examiner—Scott R. Allers
Attorney, Agent, or Firm—Browdy and Neimark

[57] ABSTRACT

The behavioral tendencies of a system in which responses evoked by stimuli are measurable are determined by means of a method and apparatus for applying a train of paired stimuli to the system and measuring and analyzing the response. The first of each pair of stimuli (conditioning stimulus) is applied at randomly varying intensities and at a constant interval. The second of each pair of stimuli (test stimulus) is applied at a constant intensity and a randomly varying interval from its associated test stimulus. By appropriate analysis of the amplitude and latency of the evoked responses, important information about fatigue, refractory period, supernormal period, threshold and dynamical fluctuation can be determined.

25 Claims, 17 Drawing Sheets

WAVEFORM DISTORTION DUE TO RESPONSE FATIGUE

WAVEFORM DISTORTION BY AVERAGING DUE TO RESPONSE FATIGUE

RANDOMIZED PAIRED STIMULUS PARADIGMS

RANDOMIZED PAIRED STIMULATION APPROACHES

SPLIT ROOT PREPARATION TO SHOW AXON-AXON INTERACTIONS

INTERACTIVE RANDOMIZED PAIR STIMULI.

INTERACTIONS BETWEEN ADJACENT DORSAL COLUMN AXONS

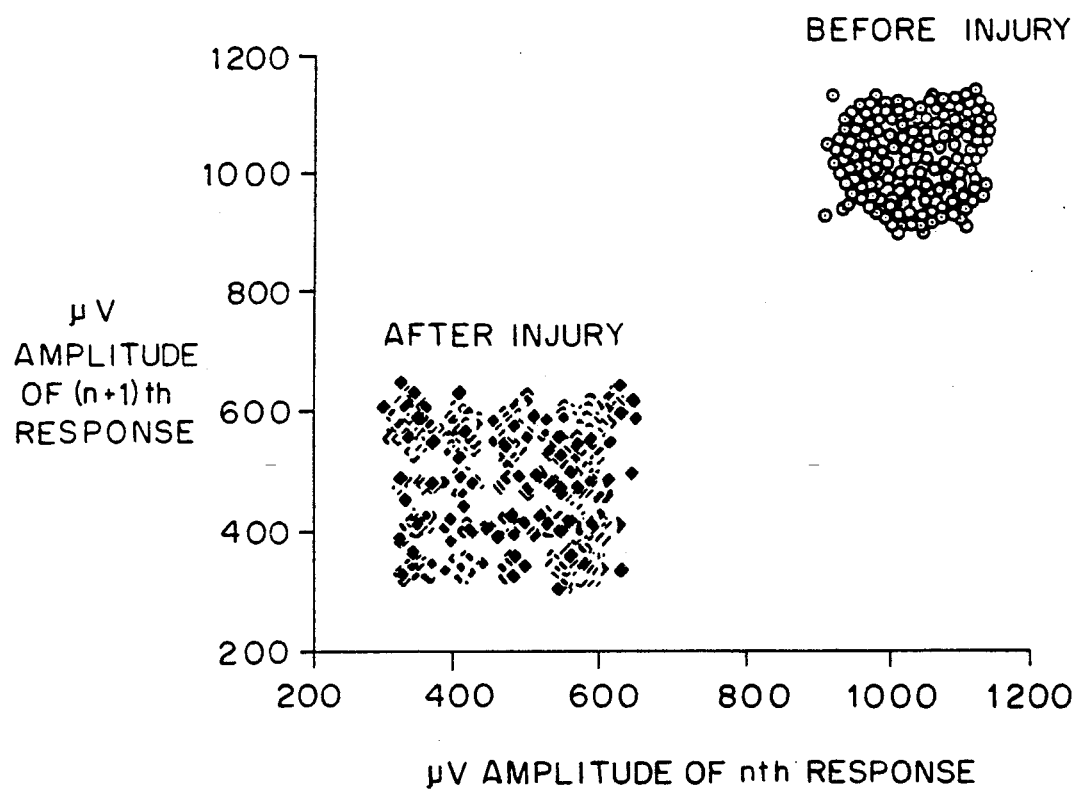

BLOCK DIAGRAM OF DATA ANALYSIS

DORSAL ROOT PERIPHERY NERVE

BEFORE DR INJURY

AFTER DR INJURY

DORSAL ROOT PERIPHERY NERVE

FIG. 17

COMPARISON OF THE DORSAL COLUMN CAP AMPLITUDE AT 12.5-125 Hz AFTER SPINAL CORD INJURY

| No. of Response | 8 msec<br>mean ± SD(uV) | 10 msec<br>mean ± SD(uV) | 20 msec<br>mean ± SD(uV) | 30 msec<br>mean ± SD(uV) | 50 msec<br>mean ± SD(uV) | 80 msec<br>mean ± SD(uV) |
|---|---|---|---|---|---|---|
| 1-20 | 564.8 ± 13.5 | 586.9 ± 12.4 | 608.6 ± 14.6 | 601.3 ± 15.3 | 596.3 ± 20.3 | 592.9 ± 18.7 |
| 21-40 | 559.3 ± 9.5 | 578.6 ± 9.8† | 589.8 ± 10.0† | 585.0 ± 10.3† | 574.5 ± 9.4 | 561.4 ± 12.0 |
| 41-60 | 556.0 ± 8.8 | 572.3 ± 12.1 | 585.9 ± 11.1† | 582.2 ± 9.3† | 564.9 ± 15.5 | 555.3 ± 19.3 |
| 61-80 | 557.9 ± 10.7† | 568.8 ± 11.6† | 586.7 ± 9.1† | 582.8 ± 16.4† | 561.0 ± 10.5† | 540.5 ± 11.6 |
| 81-100 | 553.7 ± 9.0 | 569.0 ± 8.9† | 587.5 ± 9.2† | 572.3 ± 17.3† | 560.5 ± 9.5† | 544.0 ± 13.4 |

† : $<0.01$ (paired t-test)

RANDOMIZED DOUBLE PULSE STIMULUS AND PAIRED EVENT ANALYSIS

FIELD OF THE INVENTION

The present invention relates to methods and apparatus for quantifying thresholds, fatigue, refractory, supernormal, and fluctuating responses of biological or non-biological systems, to randomized paired stimuli or events. The present invention further relates to methods and apparatus for measuring and displaying interactions of responses evoked by different paired stimuli or events in these systems.

BACKGROUND OF THE INVENTION

Conventional methods for assessing stimulus-evoked or event-related responses in biologic systems emphasize averaging responses to stimuli or events repeated at constant frequencies. In the case of the nervous system, for example, neurons generate electrical signals after stimulation of peripheral nerves, such as in the retina, the cochlea, or skin receptors. Recorded from the body surface, neurophysiological responses are as small as 10 microvolts ($\mu V$) compared to background electrical noise which may be 100 $\mu V$ or greater. To resolve signal from noise, it is often necessary to average multiple responses in the time domain. Signal averaging is based on the principle that all electrical potentials that are not time-locked to the stimuli will tend to cancel while electrical responses time-locked to the stimuli will not. To obtain multiple responses for averaging, stimuli are usually delivered as a constant frequency train of pulses at high intensities to evoke the maximum response.

One disadvantage of conventional averaging methods is that they evaluate responses to only one stimulation frequency at a time. Examining responses evoked by only one stimulation frequency may yield misleading results. For example, low frequency stimulation may produce responses suggesting apparent normality even when the system is unable to respond to higher frequency stimulations which it can normally follow. On the other hand, the system may show diminished or absent responses at a higher stimulation frequency when it is able to follow slower stimulation. These situations probably account for a majority of false negatives and false positive test results of conventional averaged evoked response tests. Although the tests can be repeated at different stimulus frequencies, most excitable systems change during repeated prolonged high frequency stimulation. The averaging process itself obscures much information contained in the individual responses. The amplitudes and latencies of averaged waveforms do not necessarily represent either the averaged amplitudes or the average latencies of the individual responses. Nor can they show trends of responses during the stimulation. These are well known and recognized limitations of conventional signal averaging methods.

Another disadvantage of conventional averaging methods is their inability to assess stimulus thresholds, especially when response amplitudes are small relative to background noise. Due to limitations of resolving signal from noise, responses resulting from lower intensity stimuli may not be detectable. Conventional evoked response methods therefore usually rely on supramaximal stimulation, i.e., using stimulus intensities beyond which there is no further increase in response amplitude with greater stimulus intensity. This inability is a serious limitation. For example, most electrophysiological tests of hearing, visual, or other sensory functions require that patients give a subjective response as to whether or not they perceive a given stimulus in order to determine stimulus threshold. Such tests would be greatly enhanced by the addition of objective means of quantifying thresholds to low-level stimuli.

A further disadvantage of conventional averaging methods is their inability to detect or quantify certain intrinsic behaviors of excitable tissues. Repeated and prolonged high frequency stimulation, as indicated above, produce response fatigue. Fatigue is when responses decrease in amplitude and increase in latency with repeated stimuli; latency is the period of time between the stimulus and the response. Excitable biological systems often exhibit distinctive post-response characteristic called "refractory period" and "supernormal period". Refractory period is the time interval after a first response during which the tissue fails to respond fully to a second stimulus and manifests in decreased amplitudes and increased latencies. Supernormal period is the time interval after a first response during which the tissue is more excited by subsequent stimuli, manifesting in increased amplitudes and decreased latencies of responses. All three phenomena may occur with repeated stimuli. Not only are conventional averaging methods unable to distinguish between these phenomena but averaged waveforms typically do not even reflect the average amplitudes or latencies of the individual responses.

Injured, perturbed, or dysfunctional systems often show marked changes in fatigability, refractory periods, and supernormal periods after responses. For example, injured spinal cords show a greater tendency for fatigue after repeated stimuli, longer refractory periods, and the appearance of supernormal behavior at lower stimulus frequencies than normal spinal cords. Likewise, people with injured retinas or impaired hearing may show greater changes to rapidly repeated light flashes and sounds. The ability of the heart to respond to electrical pacing shows characteristics of fatigue, refractory period, and supernormality. Neural, muscular, cardiac, hormonal, vascular, and renal responses to repeated pharmacological manipulations can be quite different in different disease states and in the presence of certain drugs. Such behavioral changes of perturbed systems to repeated stimuli have important clinical implications and may also provide quantifiable and objective evidence of dysfunction in situations where conventional averaging approaches show little or inconsistent changes in averaged evoked responses.

Many excitable systems exhibit characteristic fluctuations in response amplitude and latencies with repeated stimuli. The fluctuations thus may be dynamical, i.e., have a chaotic rather than a random basis. Altered fluctuations may reflect the changing contributions of multiple and complex variables in the system. Averaging and parametric statistical analysis in conventional signal analysis typically assume that the signal fluctuations are due to noise and express the fluctuations as standard deviations or errors of mean. Quantification of the fluctuation and distinguishing between dynamical changes and noise therefore may provide insight into the nature and extent of the injury or system perturbation causing altered fluctuations. Such potentially important diagnostic and prognostic characteristics of responses are obscured by conventional averaging methods.

Conventional instruments designed for stimulating and analyzing responses in reactive systems thus suffer from several major deficiencies. Because the responses are often small relative to background, averaging is typically used to resolve the response, requiring repetitive stimulation of the systems. Averaging responses evoked by constant frequency stimulation, however, obscures certain behaviors of the responses to repeated stimuli. Response fatigue, refractory, and supernormal behaviors cannot be easily distinguished from each other or quantified. Due to signal-to-noise considerations, response thresholds are often difficult to estimate when stimulus intensities and consequently response amplitudes are low. While averaging responses to repeated stimuli eliminates response fluctuations and improves signal-to-noise ratios, much critical information is lost in the process. While parametric statistical analyses can be applied to measure the magnitude of response fluctuations during the stimulation, such analyses provide little insight into the causes of the fluctuations or the relationship of the fluctuations to change in the stimulus.

Accordingly, a new and different approach of stimulating and analyzing responses is needed to circumvent disadvantages of constant frequency stimulus methods and conventional averaging approaches to evoked responses. Such an approach should be able to detect, distinguish, and quantify fatigue, refractory, and supernormal behaviors without subjecting the system to prolonged high frequency stimulation. The approach should also be able to assess stimulus thresholds for low-level signals in high noise environments and to distinguish between noise and dynamical fluctuations of responses to repeated stimuli. Finally, the approach should be compatible with existing methodologies and preferably collect and provide the same information for comparison.

SUMMARY OF THE INVENTION

It is an object of the present invention to overcome the above-mentioned deficiencies in the prior art.

It is another object of the present invention to provide methods to detect, distinguish between, and quantify the specific behavioral tendencies in response to repeated stimulation in a biological or non-biological system in which a response evoked by such stimulation is measurable.

It is yet another object of the present invention to provide methods to detect, distinguish between, and quantify the specific behavioral properties of fatigue, refractory period, and supernormal period in neural, cardiovascular, skeletal muscle, visual, auditory, secretory, renal, hepatic, gastrointestinal, genito-urinary, and other reactive systems during stimulation by repeated and varied electrical, electromagnetic, pharmacological, mechanical, thermal, hormonal, metabolic, biochemical, and other pertubations, including endogenous events that trigger responses.

It is yet another object of the present invention to provide methods to determine the thresholds of responses activated by the said repeated and varied stimuli. These include assessing thresholds of neural reflexes, pain, vestibular function, muscle contraction, hearing, vision, blood pressure, cardiac, and other tissue responses to externally imposed stimuli and endogenous events.

A further object of the present invention is to provide methods for quantifying and displaying fluctuations of responses to repeated stimuli.

It is yet a further object of the present invention to provide methods for detecting and quantifying the said behavioral properties, response thresholds, and response fluctuations resulting from interactions between two different kinds of stimuli or stimuli applied at two different sites. These include tests to quantify stereo audition and other selective hearing losses, spinal reflex interactions, color blindness, hand-eye coordination, and other functions.

Finally, it is an object of the present invention to provide apparatus for carrying out all of the above-said methods.

According to the present invention, important behavioral characteristics of reactive systems to repeated stimuli can be quantified by relating specific response characteristics to random, systematic, or uncontrolled variations of a few stimulus parameters.

The invention uses two fundamental concepts. The first is that many reactive systems display threshold tendencies have refractory and supernormal periods after responses, and fluctuate during repeated stimulation. These behavioral tendencies have critical diagnostic and prognostic implications in medical and other applications. The second is that these tendencies can be quantified by monitoring the effects of preceding stimuli or events on the amplitudes and latencies of subsequent consecutive responses.

The present invention utilizes two novel approaches to activating and analyzing responses to repeated and varied paired stimuli or events. In the first approach, pairs of stimuli are applied. The first stimulus of each pair is called the conditioning stimulus (CS) and the second the test stimulus (TS). Interstimulus intervals, CS intensities, and CS sites are varied and randomly allocated during stimulation while TS intensity and the overall frequency of paired stimuli are kept constant. The second approach applies to systems undergoing repeated, varied, and not necessarily well controlled perturbations. Perturbations of given intensity ranges are chosen to represent TS. The perturbation immediately preceding this TS therefore is equivalent to CS. Although the second approach is not strictly random, it may be considered nearly random in many situations. Thus, the term "randomized paired stimuli" (RPS) is applied to both of these approaches.

The RPS paradigm is designed to allow separate analyses to quantify fatigue, refractory and supernormal periods, conditioning thresholds, and the fluctuation of responses to repeated stimulation. Fatigue is assessed by examining the trend of CS-evoked response amplitudes during the train stimulation. Refractory and supernormal periods are determined by plotting the amplitudes and latencies of TS-evoked response to interstimulus interval. Expressing TS-evoked response amplitudes as percentages of the CS-evoked response and randomizing the interstimulus intervals provide internal controls for fatigue. Determining the minimum CS intensity that affects the TS-evoked responses gives the conditioning threshold. Response fluctuations are analyzed by examining scatterplots of consecutive response amplitudes, plotting differences between consecutive response amplitudes as a function of response amplitudes (phase-space diagrams), or dimensional analyses of the fluctuations. These analyses provide critical diagnostic and prognostic information concerning the behavior of systems to repeated stimuli.

A concept underlying the present invention is the specific analysis of response characteristics as a function of stimulus parameters. While some of the analytical approaches applied to characterizing the responses are not novel, the application of these analyses in a single automated paired stimulation protocol designed to relate response characteristics to the specific parameters is new. Some of the analytical approaches are new and have never been explained before. For example, applying a randomized paired stimulus protocol with specific emphasis on assessing refractory and supernormal periods is new. Likewise, while phase-space and dimensional analyses of response fluctuations have been carried out before, the application of these analyses have not been applied to a randomized paired stimulus (RPS) protocol. Finally, the RPS method enables more efficient investigation of stimulus parameters and response characteristics in a single automated protocol.

The stimulation and response analysis methods embodied in the present invention have the following major advantages over conventional signal averaging of responses activated by constant frequency stimulation. First, altered response thresholds, fatigability, refractory and supernormal periods, and fluctuations are sensitive indicators of system changes that are quantifiable and may show before significant waveform, amplitude, or latency shifts are apparent in conventional averaged signals. For example, mild spinal cord injuries can significantly alter fatigue, refractory and supernormal periods without necessarily altering standard evoked potential amplitudes, latencies, or waveforms. Second, conventional signal averaging obscures the causes of signal changes. The present invention specifically targets these four major causes of signal changes for quantification. Third, the analytical approaches provide data that cannot be easily obtained with currently available methods. For example, while it is possible to do averaged evoked potentials at different stimulation frequency rates, data interpretation is complicated by the absence of internal controls for response fatigue. High frequency stimulation rates not only produce fatigue but cause undesirable side effects such as pain.

While the present technique was primarily developed with biological systems in mind, it can also be applied to non-biological structures and devices such as buildings, airplane wings, tires, engines, and hydraulic systems. Such structures and devices may also show similar response characteristics to repeated perturbations. The applied stimulus may be mechanical stress, tension, torsion, etc. The response characteristics obtained using the method of the present invention can have important implications for the prediction of response and the design of such systems.

The present invention can be a standalone device, adjunct devices attached to existing instruments, or software driving general purpose computerized devices. The standalone device consists of four parts: a microprocessor based programmable stimulator, a multi-channel analog-digital converter with appropriate amplifiers, a computer with a program for data acquisition and stimulus-based analysis of multiple and simultaneous averages of responses, and an output, such as a graphic display or a stream of data to another instrument for further analysis and display. Adjunct devices include adding one or more of the four parts to conventional signal recording devices. It also can take the form of dedicated microprocessor based devices analyzing or displaying the response parameters that are described above. Finally, general purpose computers can be programmed to carry out some of the functions of RPS stimulation, data acquisition, and analyses.

BRIEF DESCRIPTIONS OF THE DRAWINGS

FIG. 1 shows the distortion of averaged waveforms due to fatigue of individual responses during constant frequency stimulation.

FIGS. 2(A) and 2(B) show the two typical patterns of randomized paired stimulation paradigms used.

FIG. 7 shows a scatterplot of the amplitudes of TS-evoked responses graphed as a function of the amplitude of the next (n+1) response.

Figure 10A:
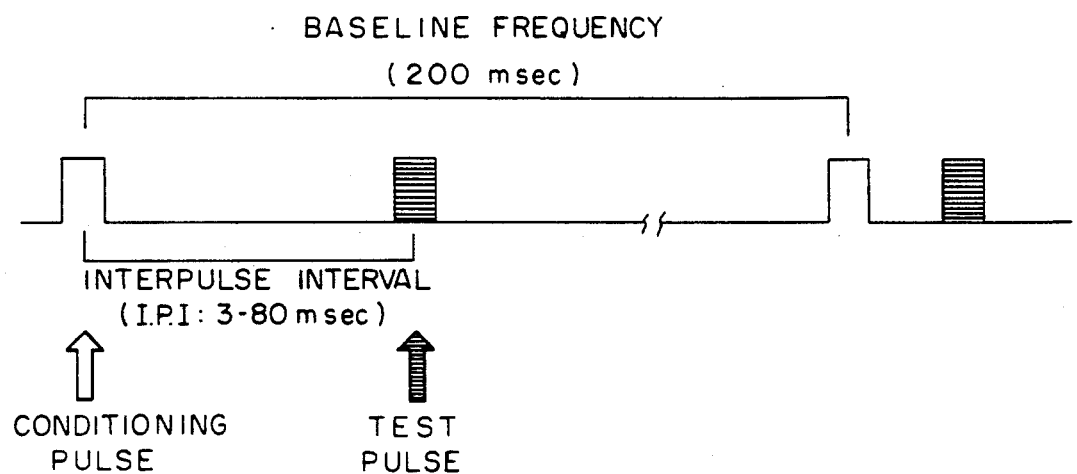

FIG. 10(A) shows a protocol of the RDP stimulation. The double pulse consisted of trains of double pulses with interpulse intervals 3–80 msec. These double pulses were delivered randomly with a fixed baseline frequency (5 Hz).

Figure 10B:
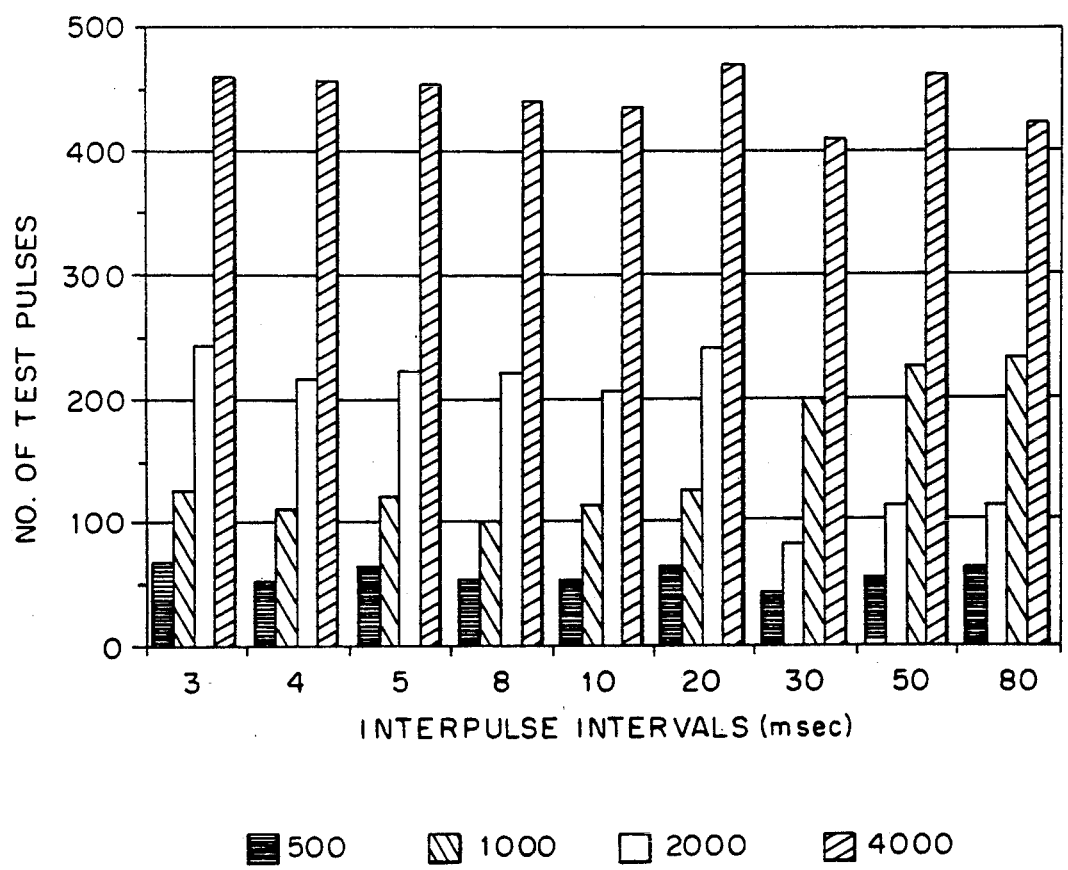

FIG. 10(B) shows the relationship between total number of the test pulses and number of the test pulses at each interpulse interval.

Figure 11A:
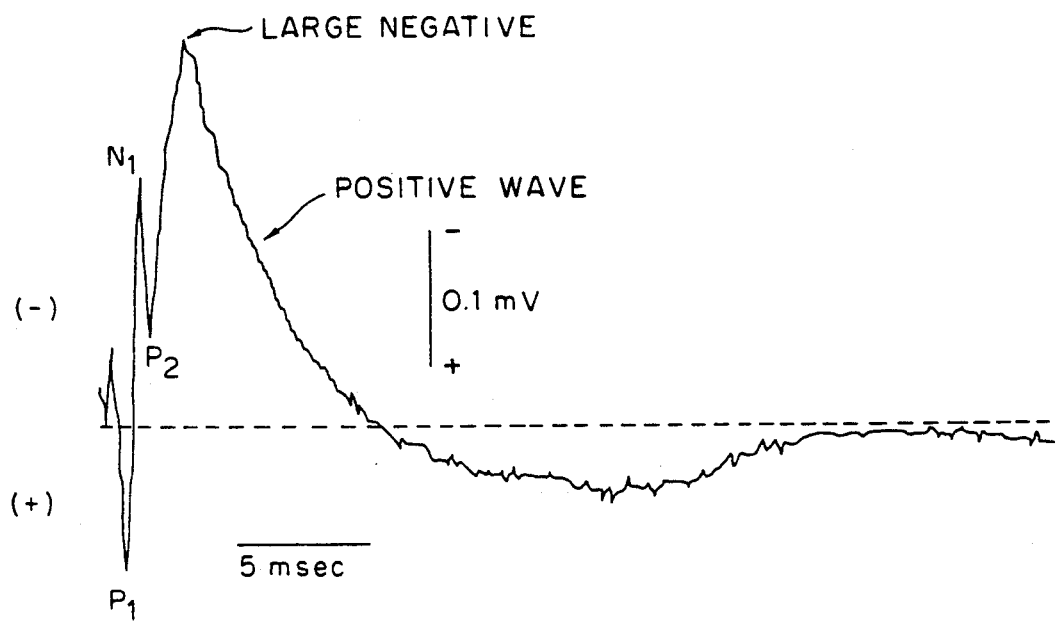

FIG. 11(A) shows the rat's cord dorsum potential recorded at 10 mm rostral to the root entry zone after L5 dorsal root stimulation. The potentials consisted of a triphasic spike and a negative wave followed by a slow positive wave. Note: positivity is downward.

Figure 11B:
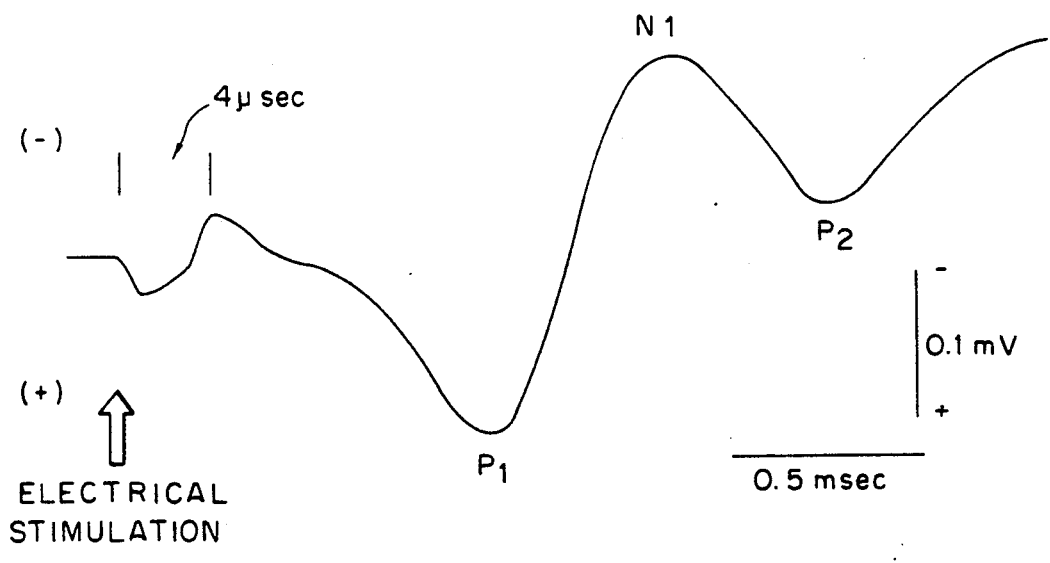

FIG. 11(B) shows the triphasic spike (dorsal column potential) in different time scale. Amplitude was measured from $P_1$ to $N_1$ and latency was measured from the stimulus artifact (white arrow) to $P_1$.

Figure 12A:
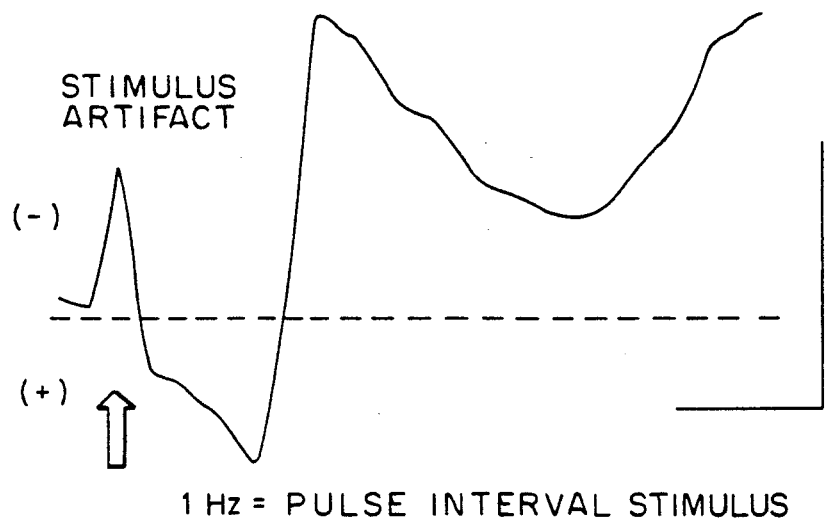

FIG. 12(A) shows the dorsal column potentials recorded above the lesion site before and after spinal cord compression injury (3 hours after decompression). These are averaged potentials (n=5) evoked by L5 dorsal root supramaximally at 1 Hz. Note that the dorsal column potentials at 1 Hz show relatively small conduction changes after spinal cord injury.

Figure 12B:
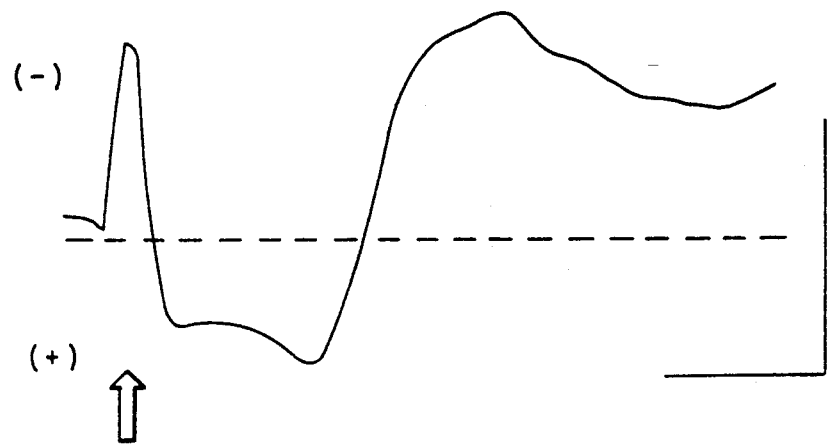

FIG. 12(B) shows the dorsal column potentials to the RDP stimulation after spinal cord injury. These are averaged potentials (n=100) at each interpulse interval. Arrows indicate stimulus artifacts. Positively is downward. Vertical and horizontal bars indicate 0.5 mV and 0.5 msec, respectively.

Figure 12C:
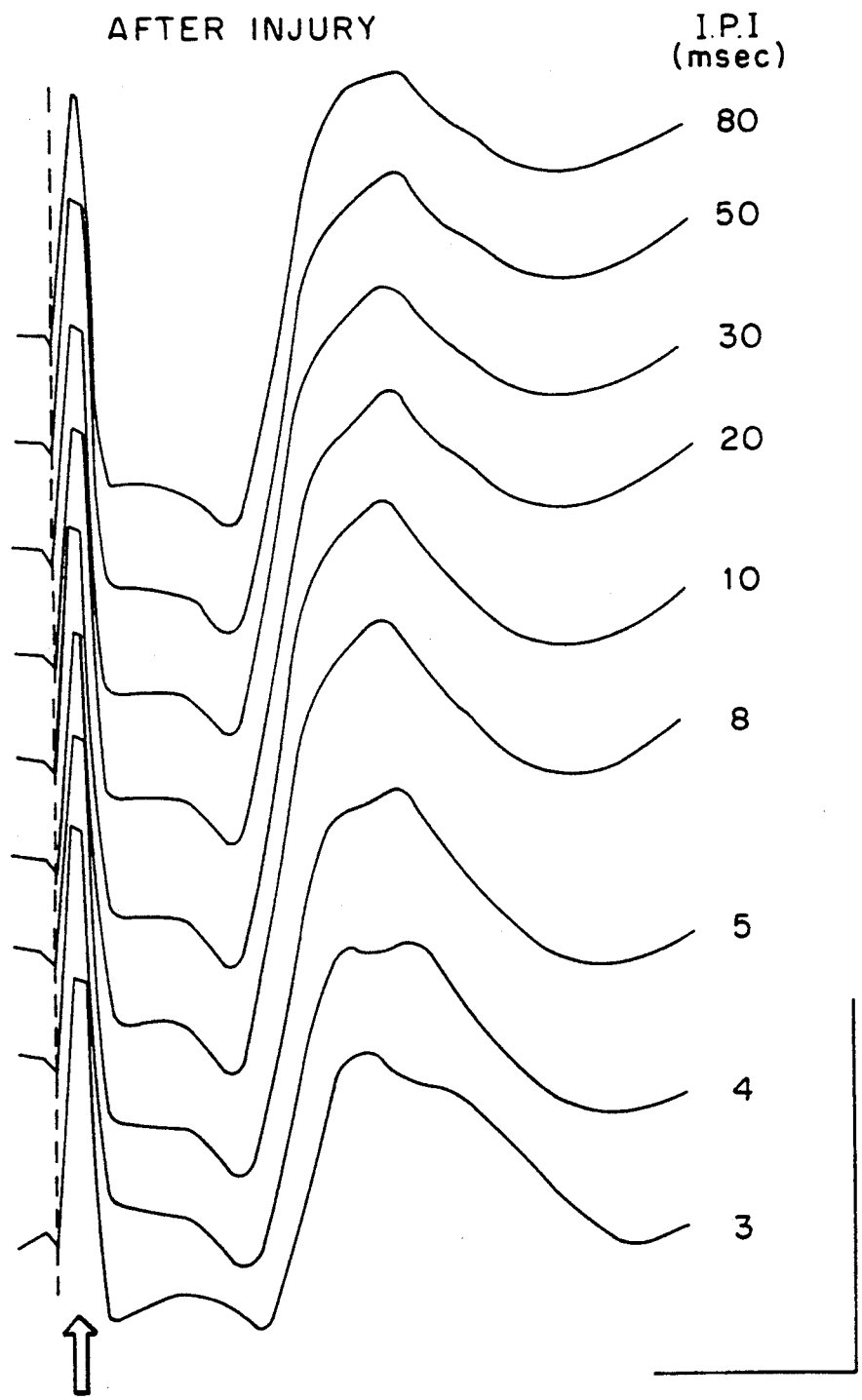

FIG. 12(C) shows multiple potentials after injury.

Figure 13A:
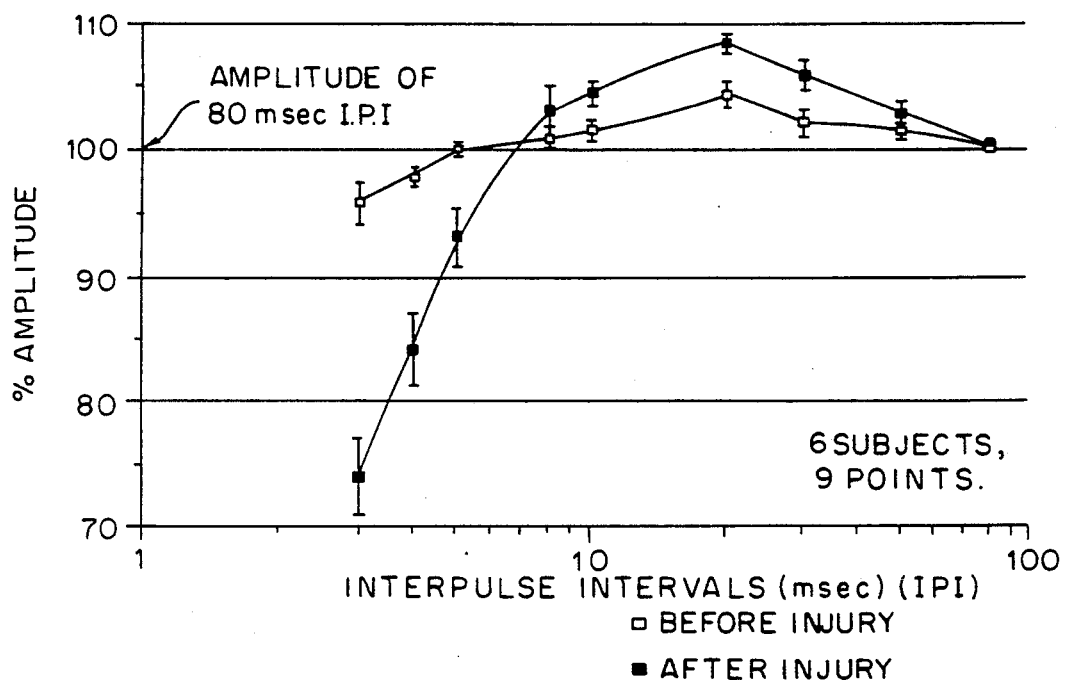

FIG. 13(A) shows the differences in the dorsal column CAP's amplitude.

Figure 13B:
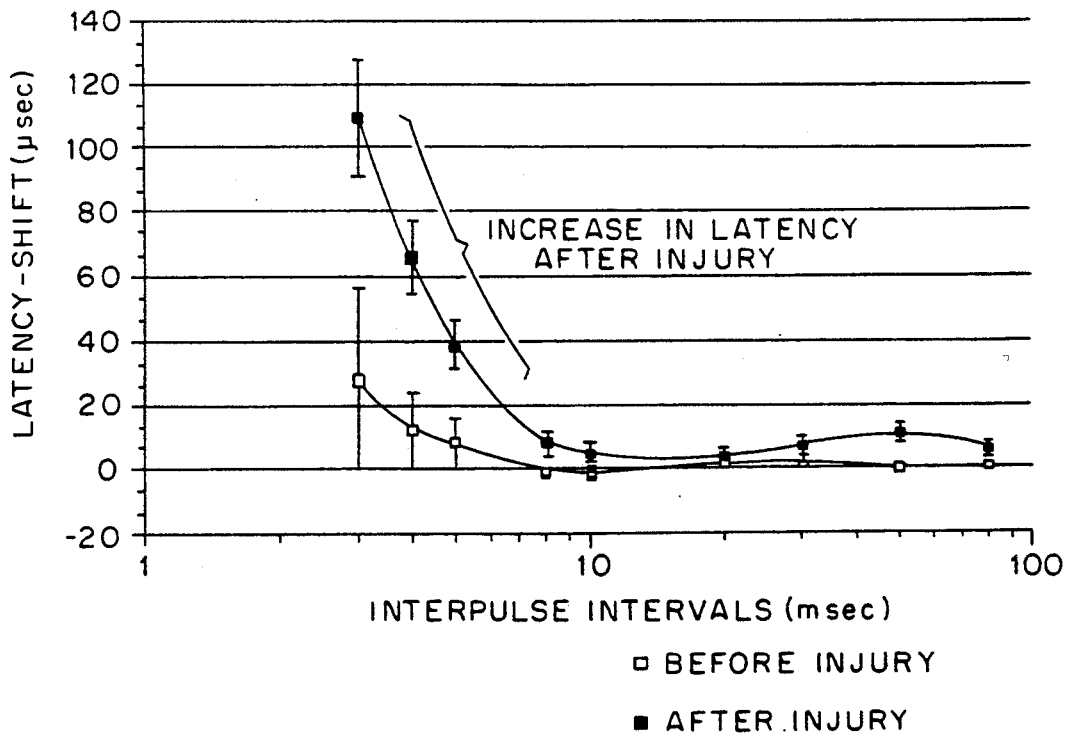

FIG. 13(B) shows latency before and after spinal cord injury in 6 rats.

Figure 14A:
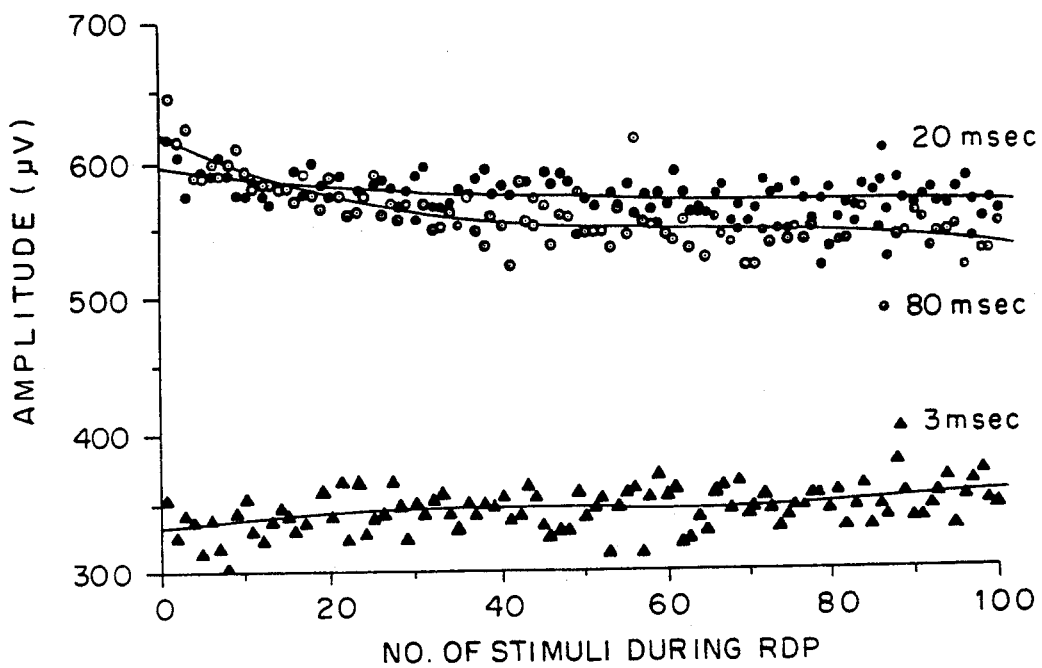

FIG. 14(A) shows changes of the dorsal column CAP's amplitude at 3, 20, and 80 msec interpulse intervals during RDP stimulation after spinal cord injury.

Figure 14B:
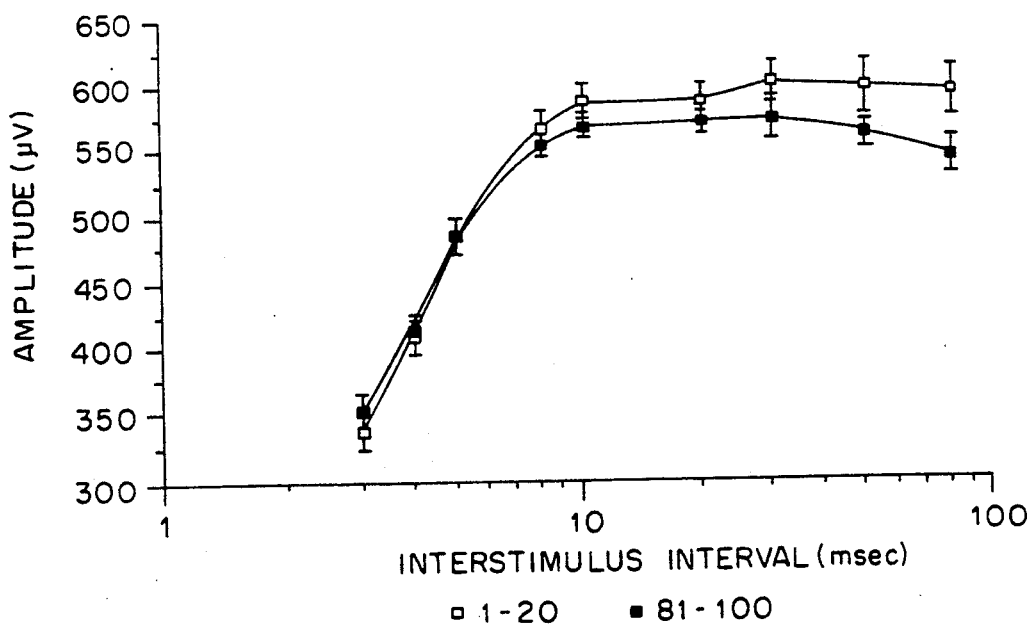

FIG. 14(B) shows averaged amplitudes of the CAPs to (1-20)th and (81-100)th test pulse of the RDP plotted against interpulse intervals.

Figure 15A:
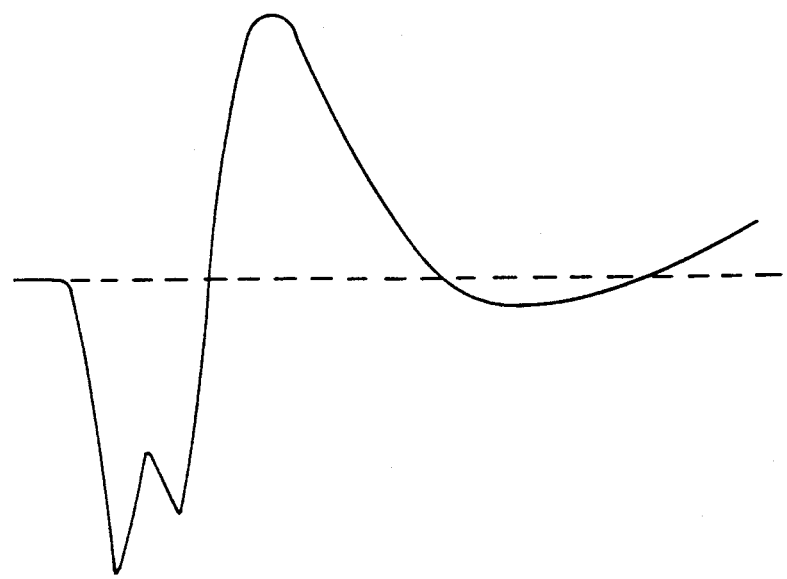

FIG. 15(A) shows the dorsal root potentials recorded above the lesion site before and after dorsal root compression injury. These are averaged potentials (n=5) evoked by L5 dorsal root supramaximally at 1 Hz.

Figure 15B:
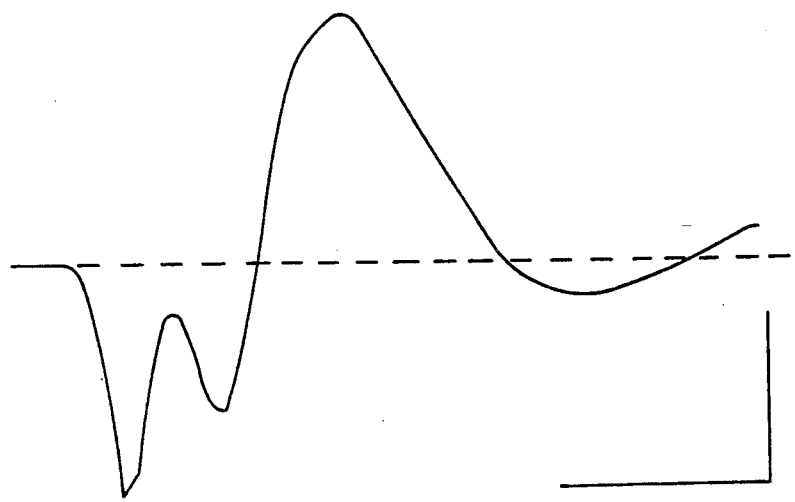

FIG. 15(B) shows the dorsal root potentials to the RDP stimulation after root injury. These are averaged potentials (n=100) at each interpulse interval. Arrows indicate stimulus artifacts. Positivity is downward. Vertical and horizontal bars indicate 0.5 mV and 0.5 msec, respectively.

Figure 15C:
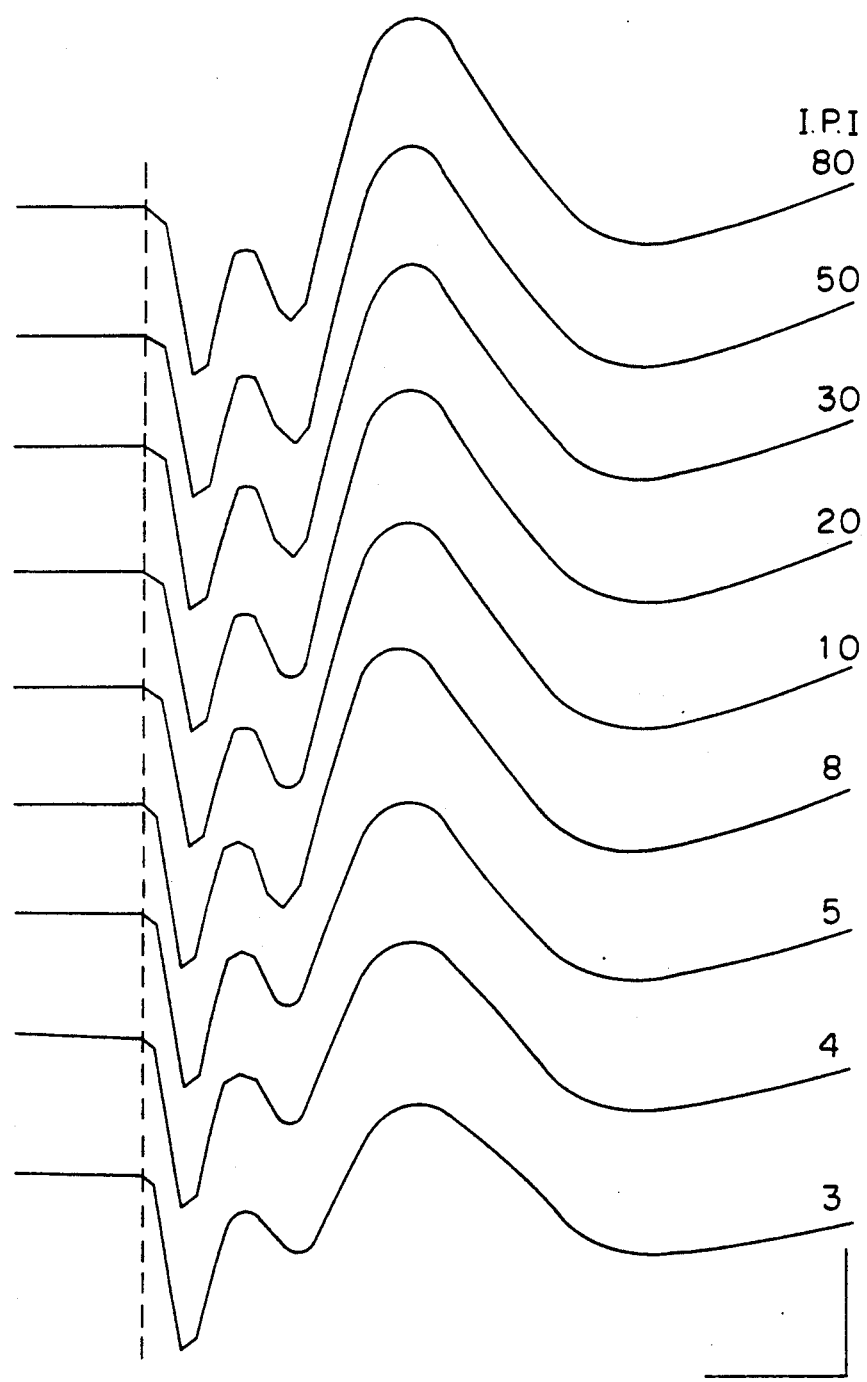

FIG. 15(C) shows multiple potentials.

Figure 16A:
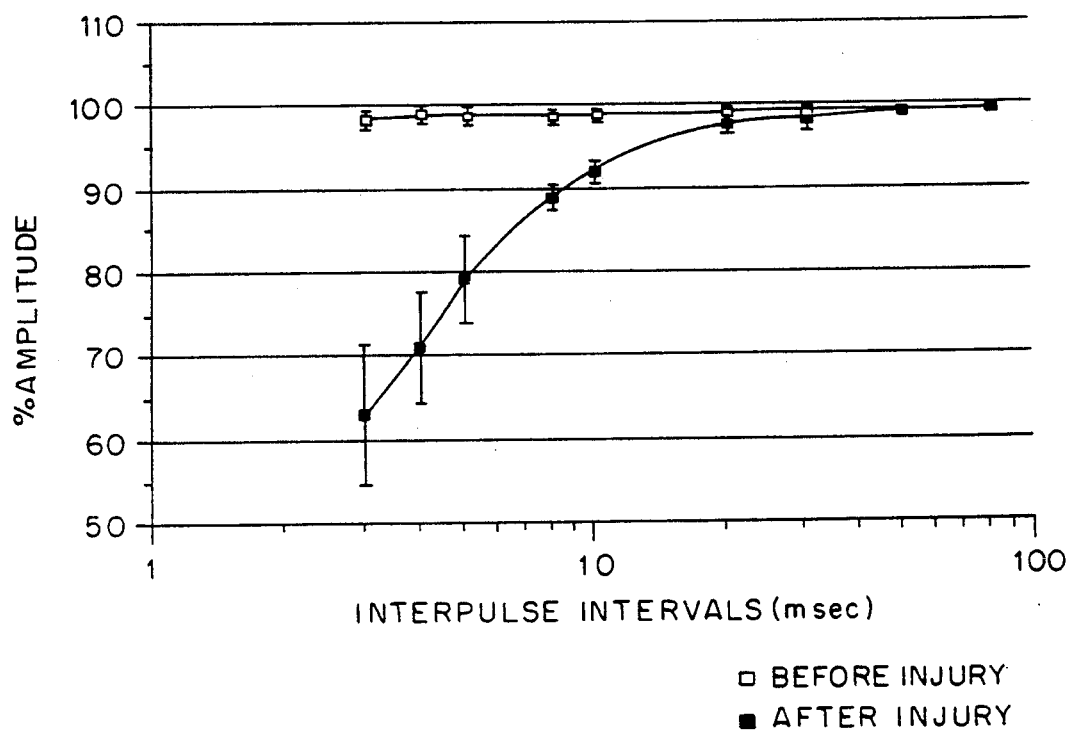

FIG. 16(A) shows the dorsal root CAP's amplitude as a function of interpulse intervals before and after dorsal root injury.

Figure 16B:
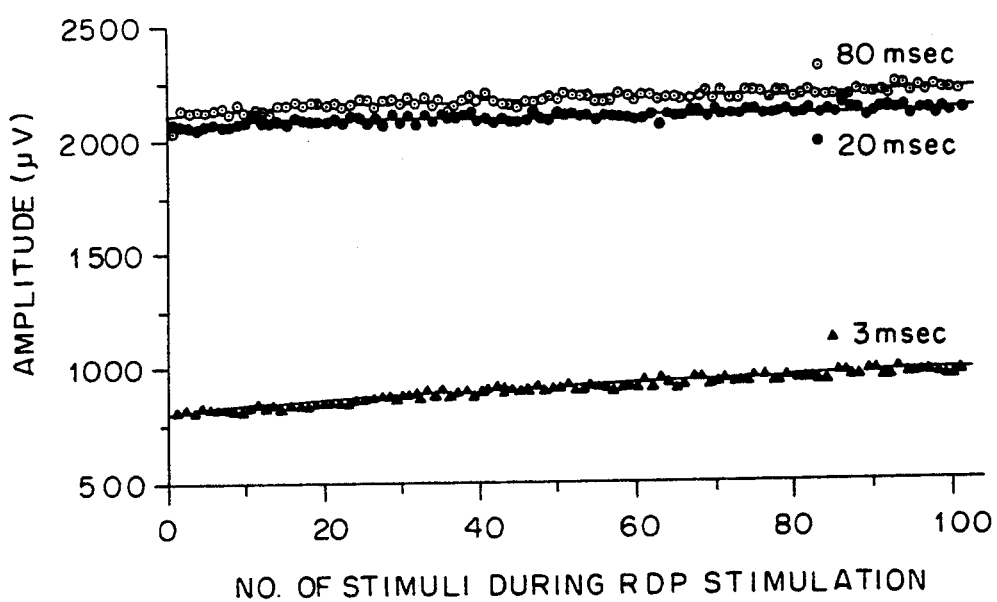

FIG. 16(B) shows changes of the dorsal root CAP's amplitude at 3, 20, and 80 msec interpulse intervals during RDP stimulation after root injury.

FIG. 17 is a table showing dorsal compound action potential amplitude data taken after spinal cord injury.

DETAILED DESCRIPTION OF PREFERRED EMBODIMENTS

Most biological systems show characteristic behavior tendencies when stimulated repeatedly. The tendencies can be summarized into five categories: fatigue, refractory period, supernormal period, thresholds, and dynamical fluctuations. For the purposes of this description, these categories are defined as follows. Fatigue is when responses decrease in excitability to further repeated stimuli after repeated stimulations, manifesting in decreased response amplitudes and increased response latencies. Refractory period is the time interval after a response during which the system has decreased excitability to a second stimulus. Supernormal period is the time interval after a response during which the system has increased excitability to a second stimulus. Threshold is a level of stimulus below which the system does not respond as much and above which the system does respond. Dynamical fluctuations are complex changes in response characteristics which are due to non-linear interactions between different processes occurring within the system and possess certain distinct characteristics that distinguish them from random noise.

To quantify these response behaviors, two approaches are used. One approach is to deliver pairs of stimuli to evoke a series of responses. The first stimulus of each pair is called CS and the second TS. TS is always maintained at a constant intensity. CS is always applied at a constant frequency, i.e., the time period between conditioning stimuli remains constant. However, the interstimulus interval between CS and TS is varied. CS intensity and sites can also be varied. These stimulus variations are randomly allocated during the stimulus train.

The second approach is to measure repeated perturbations that occur spontaneously and the responses to these perturbations. Perturbations which are within a certain small intensity range will be designated TS and the immediately preceding perturbations will be designated CS.

If the individual TS-evoked responses are small relative to background noise and require averaging to resolve signal from noise, the responses are averaged separately for discrete categories of interstimulus intervals and CS intensities. Otherwise, the individual responses are individually compared against stimulus parameters as continuous variables. Refractory and supernormal periods are determined by examining the effects of interstimulus interval on the amplitude and latencies of the TS-evoked response. Fatigue is assessed by examining trends of response changes during the stimulation. Conditioning thresholds are determined by examining effect of different CS intensities on the TS-evoked potential. The patterns and dimensions of response fluctuations during the stimulation are measured and related to stimulus parameters. Six analytical approaches are described below.

1. Fatigue Analysis

The latencies and amplitudes of individual TS-evoked and CS-evoked responses are plotted as a function of the stimulus pair number. Fatigue is defined as the tendency of responses to wax or wane during repeated stimuli. Although fatigue is probably caused by the same mechanisms that produce refractory periods, different or additional mechanisms may be involved. Regression analysis is carried out to determine if a significant trend for fatigue or supernormality occurs during the stimulation.

Figure 3:
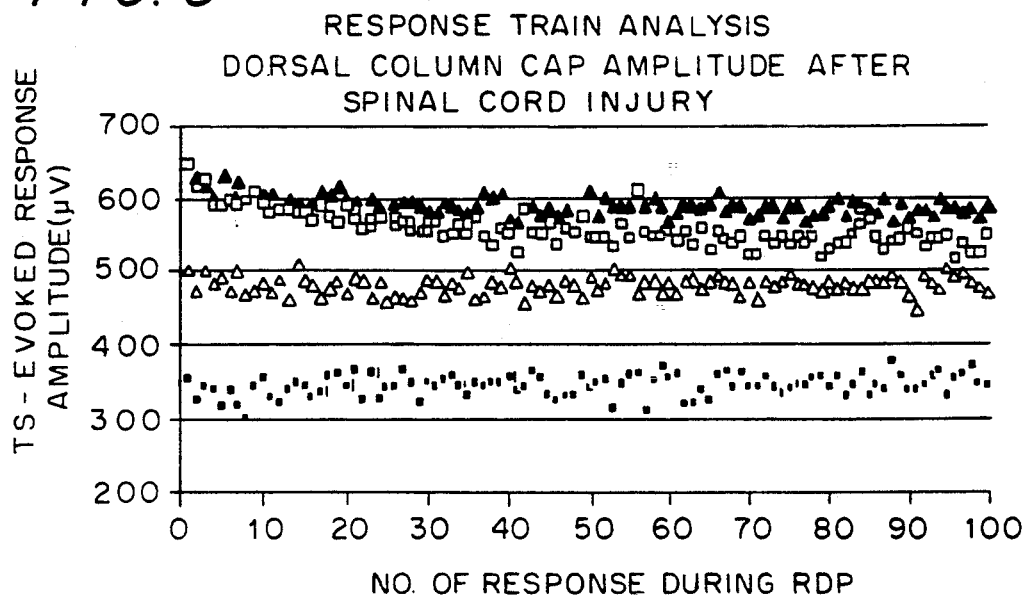
FIG. 3 shows a typical response train (RT) analysis of responses.

FIG. 3 illustrates a response train (RT) plot of TS-evoked response amplitudes during a sequential stimulus train. The regression analysis can also be carried out on TS-evoked responses expressed as a percentage of CS-evoked response amplitudes for several different interstimulus frequencies. Such an approach will detect and quantify fatigue in the TS-evoked responses for specific categories of interstimulus intervals, CS intensities, and CS sites.

2. Refactory and supernormal period analysis

Figure 4:
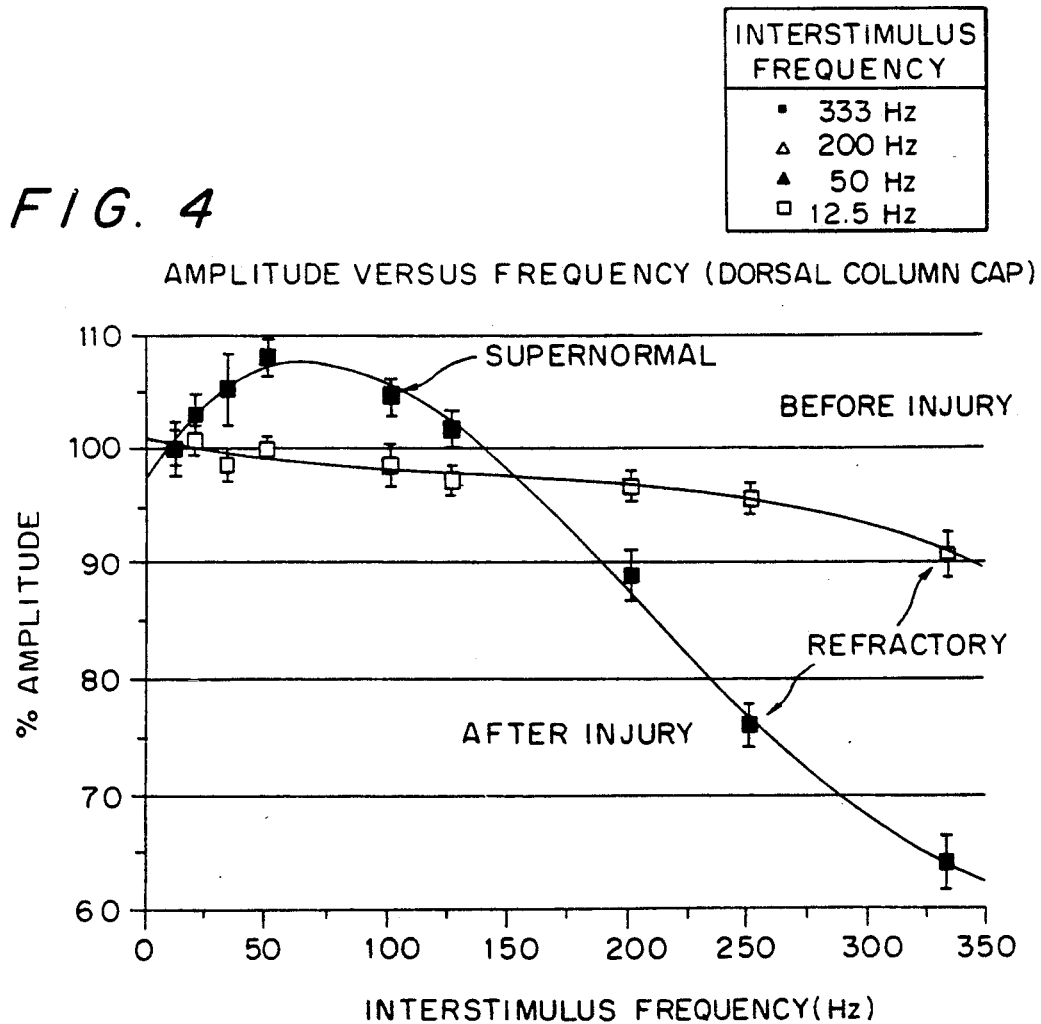
FIG. 4 shows a typical amplitude versus interstimulus frequency plot.
Figure 5:
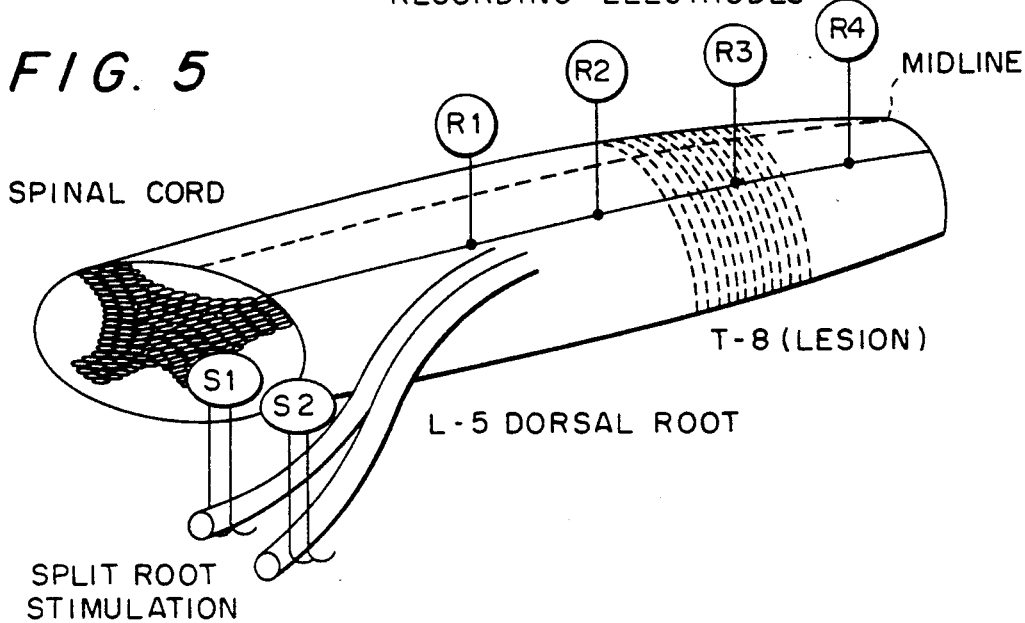
FIG. 5 shows a diagram of the split root preparation used to show axon-axon interactions in the spinal cord and to illustrate the use of the interactive randomized pair stimulation paradigm.

The responses in each interstimulus-interval but same CS intensity are separately averaged. The amplitudes of the averaged responses are expressed as a percentage of the CS-evoked responses and then plotted as a function of interstimulus frequency, the inverse of interstimulus interval. This amplitude-frequency (AF) plot will show the refractory period and supernormal period, corrected for fatigue during the stimulation, as shown in FIG. 4. Similarly, latency can be used. The average latency difference between the CS-evoked and TS-evoked responses are calculated and plotted against interstimulus frequency. This latency-frequency (LF) plot will also show refractory and supernormal periods. Generally, latencies increase in refractory periods and decrease in supernormal periods.

3. Conditioning Threshold Analyses

The responses in each interstimulus-interval and CS intensity category are averaged or analyzed individually. The amplitudes are expressed in percentage of CS-evoked responses and then plotted as a function of CS intensity to obtain the conditioning threshold (CT). CT is defined as the minimal CS intensity that has a significant effect on subsequent TS-evoked response amplitude or latencies. By definition, in order for CS to have a significant effect on TS-evoked responses, TS must occur during the refractory or supernormal period. CT is not necessarily the actual threshold of the response. However, if a given CS intensity significantly alters TS-evoked responses, the CS stimulus must have activated the system to some degree.

4. Scatterplot analysis.

The amplitude or latency of each (nth) TS-evoked response is expressed as a percentage of the CS-evoked response and plotted against the amplitude or latency respectively of the next (n+1th) response. This plot gives a unique perspective of the fluctuations of consecutive responses. FIG. 7 shows an example of such a scatterplot, amplitude fluctuations in conducted compound action potentials in dorsal column of a rat before and after injury.

5. Amplitude Dependent fluctuations.

Evoked responses are recorded in the time domain and expressed in signal amplitude at progressive time intervals after stimuli. Individual evoked response are separately converted into plots of amplitude changes (ΔAmp) versus amplitudes (Amp) of each time point of the TS-evoked response. ΔAmp is calculated from the slope of amplitude change within stipulatable time intervals surrounding each time point. Amp is calculated from the average of amplitude within stipulatable time intervals surrounding each time point. The resulting plot yields a two dimensional display of the relationship between ΔAmp and Amp. This analysis identifies amplitude-dependent fluctuations of th response. Amplitude-dependent fluctuations are very sensitive detectors of injury. In injured spinal cords, for example, action potential fluctuations show distinctive grouping patterns of amplitude-dependent fluctuations produced by different interpulse intervals. These groupings are pathognomonic for specific axonal conduction disorders. Specific applications for such displays include tests for spinal conduction in diseases like multiple sclerosis, spinal reflexes for spasticity, assessment of muscle fatigue and contraction properties for the purposes of grading physical therapy or sports training programs, and assessment of the smoothness of task performance by subjects or machines.

6. Dimensional Analyses

The fluctuations of the responses will also be assessed using the following method. Dimensional analysis is a means by which dynamical fluctuations can be distinguished from random noise. If the fluctuations are not random, the analysis yields a dimensional value which is an estimate of the number of independent variables contributing to the fluctuations. For this analysis, individual amplitude points at different times after stimulus are viewed as vectors representing the amplitude differences between that individual point versus all other points in the response. The number of such vectors separated by distances of less than r, i.e. n(r), changes as a function of r. Theoretically, the scale of the vector number is:

$$n(r) \simeq r^d$$

where d is the correlation dimension of the set, obtained by the following $$\log n(r) = d \log (r)$$

The value of d is estimated from the slope of the plot of log n(r) versus d log (r). The steeper the slope, the greater the dimensions of the system. Clearly, if the fluctuations are purely random, the correlation coefficient of the two variables should not be significant. On the other hand, because there is a finite limit to the resolution of the acquired data, due to analog to digital conversion and other limitations, some random noise may appear to have a dimension. For that reason, the instrument will also collect some no-stimulus responses, scattered randomly within the stimulus train. Finally, because of the finite size of vectors in the multidimensional construct the relationship of log n(r) versus d log (r) will be linear only within certain regions and the linear regression will be restricted to values of r determined algorithmically. Due to these limitations, the calculated dimension value will be called by the more cautious term of "complexity parameter". Dimensional analysis provides insights into the complexity of the variables contributing to response fluctuations under different stimulus conditions. The complexity parameters are plotted against the different stimulus parameters.

Figure 1:
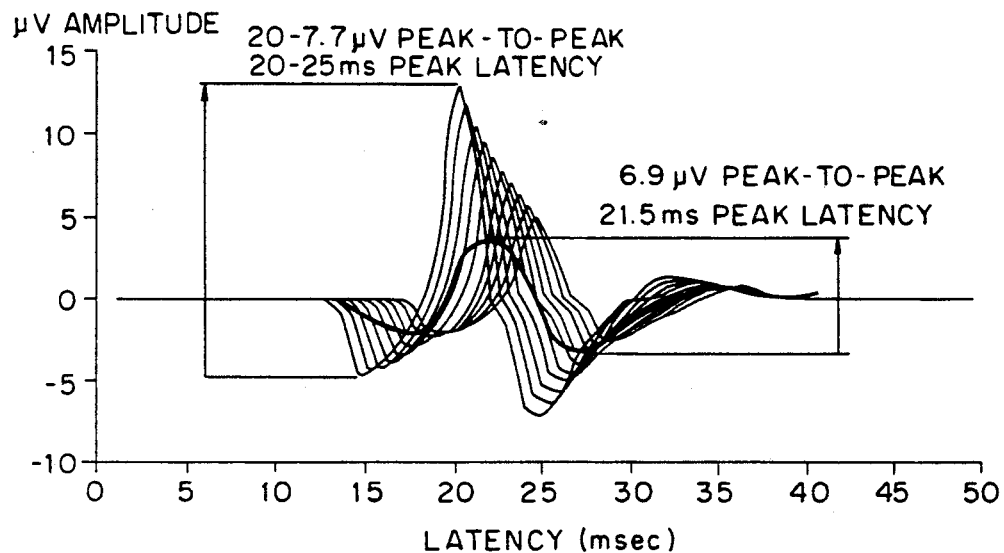

In FIG. 1, typical individual triphasic waveforms are shown with lighter lines. Progressive decreases in peak-to-peak amplitude from 20 to 7.7 μV and progressive delays of peak latencies from 20 to 25 msec are shown. The averaged waveform, shown in the heavy line, is not only a distorted representation of the individual responses but the peak amplitude and latency of the averaged waveform does not match the average amplitudes and latencies of the individual responses.

Figure 2A:
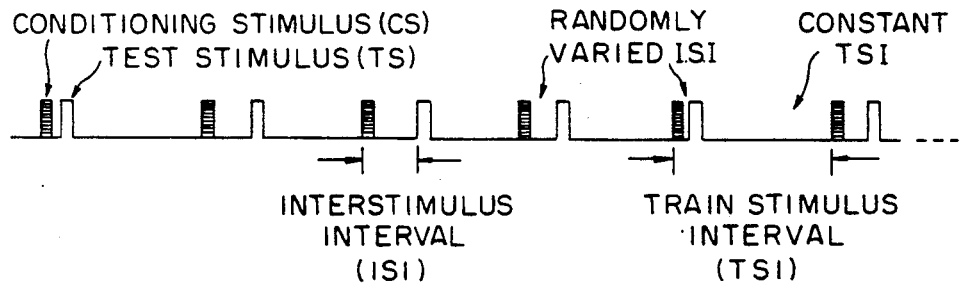
Figure 2B:
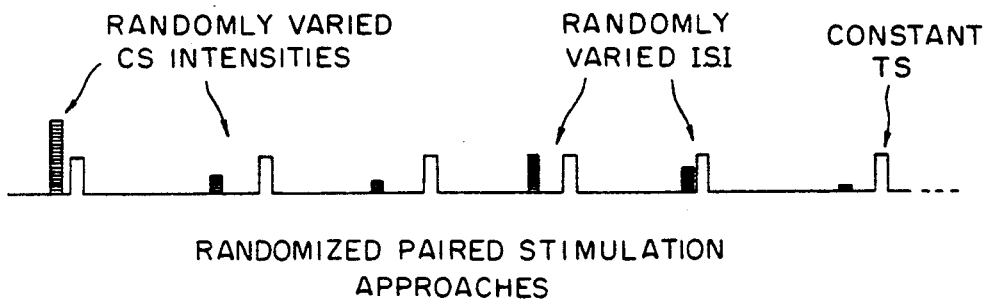

In FIG. 2, "A" represents the randomized interstimulus interval (ISI) stimulation paradigm. "B" represents the randomized conditioning stimulus (CS) intensity and ISI paradigm. In both, test stimulus (TS) intensity and train stimulus interval (TSI) are maintained constant. The former is what would be used if only RT, LAF, and N:N+1 analyses were to be carried out.

In FIG. 3, a response train analysis is carried out on compound action potentials (CAP) recorded from the spinal dorsal column in response to RPS applied to a lumbar dorsal root (L5) in rats. Only the amplitudes (AMP) of TS-evoked responses are shown (μV). Four categories of interstimulus intervals were used and expressed as the inverse of interstimulus interval, which is the interstimulus frequency (12.5-333 Hz). Note the tendency of the 12.5-50.0 Hz points to fall with time after onset of the stimulus train. This is due to fatigue.

In FIG. 4, a typical amplitude versus interstimulation time plot is shown. Nine categories of interstimulus frequencies were applied to the L5 dorsal root. Dorsal column compound action potentials were recorded from the spinal cord. The amplitudes of the test-stimulus (TS) evoked responses are given as the average percentage of the amplitudes of the responses evoked by the conditioning stimulus (CS). The error bars indicate standard deviations. Before injury, the responses did not change significantly at interstimulus frequencies of 10–100 Hz but decreased progressively and slightly by about 10% between 100–350 Hz. After stimulation, the responses increased significantly between 50–100 Hz and then declined precipitously between 100–350 Hz.

Figure 6:
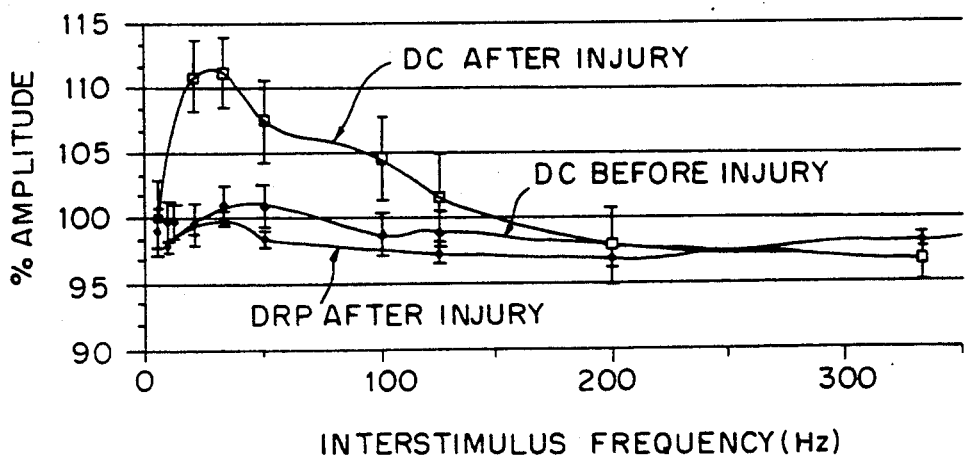
FIG. 6 shows an amplitude versus interstimulus frequency plot of an interactive RPS study shown in FIG. 5.

In FIG. 6, the amplitudes of the TS-evoked responses are expressed as a percentage of CS-responses. Before injury, there was no significant interaction between responses activated stimuli delivered to these two sites with interstimulus frequencies from 10–333 Hz. After injury, however, there was a highly significant interaction at 10–120 Hz interstimulus frequencies. Note the absence of a refractory period, indicating no spread of current from the CS stimulation site to the TS stimulation site.

In FIG. 7, a typical scatterplot of nth versus n+1th response amplitudes is shown. Before injury, the points are clustered in the upper right corner and fairly uniformly distributed. These amplitude data are the same as those shown in FIG. 3. After injury, the points not only cluster to the lower left but show a distinct pattern. Each group of points represent 1000 responses.

At the same time that this analysis (six analytical approaches listed above) is carried out, the device can collect conventional averaged evoked potentials. The CS-evoked responses are averaged in the time domain, omitting the responses where the TS-evoked response enters the time domain of the CS-evoked response. This is essentially equivalent to the standard average evoked responses except that the stimulus delivery rate is slightly variable.

While many of the signal analysis techniques are established methods of signal analysis, the implementation of these analytical approaches within the framework of a generalized paired stimuli or events paradigm is new. Most previous applications of dimensional analyses have focussed on spontaneous activity of reactive systems, such as the nervous system and the heart. This invention applies analytical techniques to paired stimuli paradigms.

The present invention has a wide range of medical applications which include assessments of sensory (visual, auditory, somatosensory, pain, vestibular, etc.) thresholds and function; muscle performance, strength, and fatigue; abnormal neural responses in multiple sclerosis, spinal cord injury, and other neurological conditions; cardiac output and response to pacemaking devices; responses to repeated pharmacological treatments; vascular contractility; blood pressure responses; renal function; gastrointestinal function; hormonal and metabolic responses to endogenous or exogenous events; bladder function; spinal reflexes; anesthetic levels; and others The medical applications are too numerous to be described individually. Examples will be given below to illustrate some major applications. Many of these applications are well suited for use in children, comatose or otherwise incapacitated adults who cannot cooperate voluntarily, and animals.

1. Neural Evoked Potentials.

a. Normal neurophysiological investigation.

Pathways in the brain and spinal cord are activated by stimulation of peripheral nerves, receptors, or direct stimulation of the central nervous tissues. The responses are recorded from the body surface or directly from the neural structures. RPS trains with variable interstimulus intervals and varied CS intensities are used to activate the responses. Amplitude-frequency and latency-frequency plots will characterize the behavior of these pathways. Amplitude versus conditioning stimulus intensity plots will illustrate the conditioning stimulus threshold. Depending on the pathway between the stimulation point and the recording point, amplitude-frequency and latency-frequency plots may show markedly different patterns. In addition, averaging the CS-evoked responses will yield the same information as a conventional averaged evoked potential.

b. Pathological neurophysiological studies.

Conduction in injured or demyelinated axons tend to show increased fatigue and refractory periods at high stimulus frequencies. In addition, injured axons often show supernormal excitability at certain stimulus frequency ranges. Some of these behaviors are pathognomonic for dysfunctional axons. Thus, use of the RPS paradigm and response analysis will give insights into the degree and type of injury in peripheral nerves and spinal cord white matter pathways. Likewise, synaptic transmission may show alterations in fatigue, refractory periods, and supernormal behavior in injured systems. RPS assessment of axonal conduction is also a more sensitive and quantitative test of neural dysfunction than conventional evoked potentials and will be useful for early detection of disease states. 2. Visual Function Tests.

Conventional visual evoked potentials methods utilize either light flashes or a shifting checkerboard pattern to activate visual cortex responses recordable from the occipital cortex. Such stimuli usually produce relatively low level signals which cannot be used to determine stimulus thresholds accurately.

a. Central visual pathways.

Central visual pathways can be tested using the RPS paradigm. RT analyses will reveal the presence of fatigue. LAF plots will show refractory periods and the presence of supernormal periods (if any). LAC plots will show the threshold at which the CS-evoked responses alter the TS-evoked responses.

b. RPS electroretinogram studies.

Light flashes activate retinal responses that can be recorded with electrodes situated close to the orbit. These responses represent the mass activation of large numbers of sensory and other neural elements in the retina. Use of RPS paradigm will allow quantification of the response behavior, as well as the threshold of CS intensity necessary to alter TS-evoked responses.

c. Color vision tests.

By setting the CS at a different color from TS, it is possible to apply RPS to see the effects of a prior differently colored light pulse on a test retinal response. This allows quantification of selective color blindness. For example, if a subject is insensitive to blue. A blue CS should result in less than normal change in the electroretinogram or cortical evoked response to white light, i.e., no refractory period. By lowering the intensity of the blue CS until no effect is seen in the TS-evoked response, it is possible then to quantify the degree of color insensitivity of the subject without requiring any subjective perception by the subject. 3. Muscle Function Tests.

Muscle weakness is commonly evaluated clinically by having the subject voluntarily move and the strength of the movement is graded subjectively on a scale of 1 to 5. Mechanical devices can be utilized to measure the strength of voluntary contractions. Alternatively, electromyographic (EMG) responses can be recorded after stimulation of the peripheral muscle supplying the muscle. Because EMG responses are large, response thresholds can be readily determined. However, certain characteristics of the muscle response cannot be conveniently measured. For example, fatigue and ability of the muscle to follow high frequency stimulation are difficult to quantify. Furthermore, subtle changes in muscle performance cannot be easily detected. RPS paradigms and analytical methods will greatly enhance the information obtained concerning muscle performance.

a. Muscle performance assessments.

Trains of RPS are delivered to the peripheral nerve supplying the muscle being recorded from. LAF plots will show the refractory period and any supernormal period. RT analyses will allow quantification of muscle fatigue. N:N+1 scatterplots (FIG. 7) and dimensional analyses will provide a measure of the consistency of the response to different stimulus parameters. These measures will be particularly useful for grading the efficacy of sports training programs and physical therapy exercises, for example.

b. Tests of neuromuscular transmission.

In operating rooms, patients are often paralyzed with various agents. The effects of these drugs on neuromuscular transmission can be quantified with RPS. Also, such tests may be useful for early detection of myesthenia gravis in patients who do not show gross weakness. 4. Auditory Function Tests.

Conventional audiograms require subjects to tell the examiner whether they perceive a given auditory signal. The test is time consuming and necessitates a cooperative subject. The test is not easily applicable to very young, comatose, malingering, or anesthetized patients. Alternatively, it is possible to do brainstem auditory evoked responses (BAER) by applying tone pips and recording the early brainstem responses to the stimuli. Since BAERs are very small signals, the test cannot be used to determine hearing thresholds or mild selective hearing losses. The RPS paradigm and response analyses, however, will test these functions and provide much additional information.

a Audiogram without Interaction.

By examining the threshold at which CS-evoked responses alter TS-evoked responses over a wide intensity and frequency range, a complete audiogram can be obtained in an uncooperative, comatose, or anesthetized subject. The interactions of different frequency and intensity tone pips can be examined and assessed quantitatively. In addition, because the responses typically have short refractory periods and do not tend to fatigue, it is possible to test a wide range of frequencies and intensities very rapidly and carry out the test in a much shorter period of time.

b. Stereo audition.

Stereo audition can be accessed by applying the CS to one ear and the TS to the other ear. Interactions of the neural pathways between the ears can be examined. 5. Reflex testing.

Spinal and other reflexes are commonly tested in clinical examinations by mechanically stretching a tendon or otherwise stimulating sensory input to the reflex arc and observing the response in the corresponding muscle group due to reflex activity. Alternatively, the muscle response can be recorded as EMG after stimulation. RPS will greatly enhance reflex testing in the following ways.

a. Characterizing reflexes.

RPS can be easily applied electrically to selected peripheral nerves. LAF will show the fatigue, refractory period, and supernormal periods of the reflex. LAC will show the CS threshold.

b. Spasticity assessment.

Conditions such as spasticity will produce very prominent and abnormal changes in these characteristics. At the present time, there is no reliable or generally accepted methods of quantifying spasticity. Application of the RPS to specific reflex groups and reflex interactions will yield data that will allow categorization and quantification of spasticity states. Likewise, the dimensional analysis will provide a measure of the complexity of the fluctuations of reflex activity during repeated stimulation.

6. Tests of visually guided motor and vestibular performance.

The subject stands on a platform which measures the center of pressure exerted by the subject on the platform. The velocity and acceleration vectors of the center of pressure while the subject is at rest with eyes open and eyes closed ar analyzed first for the PS diagram and dimensional analysis. Pertubations of the subject's equilibrium are produced by sudden tilting of the platform. Double stimuli can be applied to determine the refractory period and detect the presence of any supernormal behavior. Dimensional analyses may reveal the presence of increased instability or decreased motor control in responses to vestibular perturbations.

7. Testing of the heart.

Conduction and excitability of the heart can be tested using the RDP method in subjects with implanted pacemakers. The RDP method is particularly suitable for the heart since very rapid stimulation of the heart will cause fibrillation and other undesirable side-effects whereas double pulse stimulations should not. Abnormalities in the spread of excitation from the atrium to the ventricles can be quantified over a wide frequency range. The method would also be applicable in situations where a stimulating catheter is placed into the heart via an intravascular route.

8. Interactive RPS studies.

a. Axonal dysfunctions.

RPS analyses show a very significant interaction between the two stimulated halves of the roots within minutes and lasting many weeks in spinal cords injured by slow compression and weight drop contusion. These data represent the first demonstration of such interactions in the spinal cord, suggesting that release of potassium ions from the action potentials in white matter affect the excitability of adjacent axons. The data strongly suggest that this is pathognomonic for demyelinated axons, since normal myelinated axons do not show that interaction. This therefore represents an additional refinement and application of the RPS to the assessment of axonal dysfunctions.

b. Spinal reflex interactions.

It is well known since the time of Sherrington that different segmental reflexes of the spinal cord interact with each other. For example, activation of any given muscle group by stimulation of the peripheral nerve will generally result in inhibition of a specific group of antagonist muscles. Although these interactions have been known for a long time, the details of the interactions have seldom been studied extensively in the clinical situation because of the tediousness of such tests. With the RPS method, it is possible to characterize completely the time course of such reflex interactions, as well as quantify the degree of interaction. For example, such tests would provide a means of assessing spasticity in subjects with lesions of the nervous system.

c. Sensory-motor interactions.

It has also been known for a long time that sensory input can alter the thresholds for motor activation in the brain. The conventional approach to studying this interaction consists of conditioning a centrally (motor cortex via magnetic or electrical stimulation) activated motor evoked potential (MEP) with a somatosensory evoked potential (SEP) activated from a peripheral nerve. Usually, only a very limited range of conditioning stimulus intervals are tested and randomization of the intervals are not carried out. The RPS method can be applied directly to assessing the time course of the interactions between sensory and motor stimuli. In addition, the conditioning threshold approach can be used to determine the level at which such interactions occur.

d. Sensory-sensory interactions.

The sensory nervous system interacts at multiple levels. It is believed, for example, that pain sensations are gated at the spinal segmental levels by cutaneous sensory input. The RPS method allows the interactions of different sensations to be tested, using somatosensory evoked potentials recorded from the spinal cord or the cortex as the output. In general, the somatosensory evoked potentials recorded from the spinal cord and cortex are dominated by electrical activity of fast conducting fibers carrying the proprioceptive and cutaneous sensations. Using the RPS method, the interaction of responses evoked by various stimuli of adjacent nerves, specific receptors, and segmentally distinct inputs can be characterized in detail. Specific abnormal patterns of interactions and responses are likely to be present in individuals suffering from pain or dysesthesia.

The RPS paradigm and response analyses of the present invention may also be used for general analyses of mechanical and electrical devices and systems. In particular, many mechanical and electrical devices display characteristics of fatigue, refractory and supernormal period, conditioning threshold, and fluctuation to repeated stimuli. Application of the RPS stimulation and response analyses to these devices and systems will allow the rigorous evaluations and prediction of the reliability, response time, and causes of device dysfunction or failure. For example, a computer data storage device such as a hard disk will show a certain failure rate over time. At the present time, the failure rate of most hard disks is sufficiently rare so that the mean time to failure is not particularly meaningful. However, detailed analyses of the devices for refractory-supernormal behavior, altered fluctuation of responses to repeated stimuli, and threshold of responses will provide an objective basis upon which to judge the reliability of such devices.

EXPERIMENTAL TEST RESULTS

The following experimental results were obtained by the testing of laboratory rat responses to electrical stimuli. They establish the validity and importance of the processes of the present invention with respect to the study of spinal cord injury.

Injury compromises the ability of axons to conduct action potentials at high frequencies. To study stimulus-frequency dependent action potential conduction characteristics in injured spinal and peripheral axons, a stimulation paradigm that applied trains of double pulses at 5 Hz and randomly varied interpulse intervals of 3, 4, 5, 8, 10, 30, 50, and 80 msec was developed. The first pulse of each double pulse was used to condition responses elicited by the second test pulse. The L5 dorsal root was stimulated to elicit dorsal column and dorsal root compound action potentials in pentobarbital anesthetized rats. The spinal cords were injured by stepwise (0.25 mm every 5 minutes) compression (5 mm from the L5 dorsal root entry zone) until action potential conduction across the compression site was abolished and decompressed the spinal cord 10 minutes later. Before injury, conditioning pulses applied 3-80 msec before test pulses did not alter dorsal column responses. Double pulse stimuli with 3-5 msec interpulse intervals significantly reduced response amplitudes and increased latencies. Injury also increased response amplitudes at 20 msec interpulse intervals compared to 80 msec intervals. Injury accentuated response fatigue during the stimulus train, manifested by decreases in response amplitudes. The fatigue was most prominent at 80 msec interpulse intervals. Spinal cord injury did not affect the dorsal root responses. Dorsal root compression depressed dorsal root action potentials at 3-5 msec interpulse intervals but did not increase fatigue at any interpulse interval. The data indicate that randomized double pulse evoked potentials are sensitive detectors of acute axonal dysfunction and ca be used to quantify stimulus frequency dependent conduction deficits in injured central and peripheral axons.

Much neuronal communication is coded in the time domain. Injury compromises the ability of injured axons to conduct high frequency impulses which severely restricts the information content of messages that these axons can deliver to their target cells. Standard evoked potential methods are insensitive to this subtle but important form of axonal dysfunction since they average responses activated at a single and usually low stimulus frequency.

Two approaches have been used to evaluate stimulus frequency dependent changes in axonal conduction: train and double pulse stimuli. In the former, trains of stimuli are applied at different frequencies and produce long-lasting physiological changes in axons and long rest periods are required between high frequency trains of stimuli. Double pulse stimulation has been found to be more suitable for determining changes in refractory periods or the ability of axons to respond to rapidly repeated consecutive stimuli.

The stimulation paradigm of the present invention combines the advantages of train and double pulse stimulation. Pairs of stimuli were delivered at a fixed baseline frequency of 5 Hz. The interpulse intervals were varied randomly between 3-80 msec. This stimulation approach allowed a direct determination of the refractory period, as well as the progressive response changes during a single stimulus train. Using this randomized double pulse (RDP) stimulation approach, stimulus frequency dependent changes in axonal conduction were examined before and after acute compression injury of the spinal cord and dorsal root of the rat.

Surgical Preparation:

Twelve adult Long-Evans hooded rats weighing 200-300 g were deeply anesthetized with 40 mg/kg pentobarbital given intraperitoneally. Supplemental doses of pentobarbital (20 mg/kg) were given intravenously every three hours or when necessary, i.e., when blood pressure rose excessively with stimulation or the animal showed responses to tail and paw pinches. After tracheostomy and intubation, polyethylene catheters were inserted into the right femoral vein for drug administration and into the left carotid artery to monitor blood pressure and gases.

The spinal cord was carefully exposed with a laminectomy from T10 to L6 segments. After mounting the rats on a stereotaxic frame (Narashige, Tokyo, Japan) with vertebral clamps to stabilize the spinal column the skin was tented around the laminectomy t hold a pool of paraffin oil. The oil was heated with a copper tube containing circulating hot water to maintain spinal cord temperatures at 36°-37° C. Rectal temperatures were monitored with a probe and maintained at 36°-38° C. with a heating pad.

To reduce the movement artifacts from muscle activation during the lumbar root stimulation, the animals were paralyzed by a dose of gallamine triethiodide (1 mg/kg intravenous) and ventilated with room air using a rodent respirator (Harvard Instruments, South Nadick, Mass.). A pneumothorax was performed to minimize spinal cord movements due to the respiration The animals were euthanized at the end of the experiments with an overdose of pentobarbital.

Figure 8A:
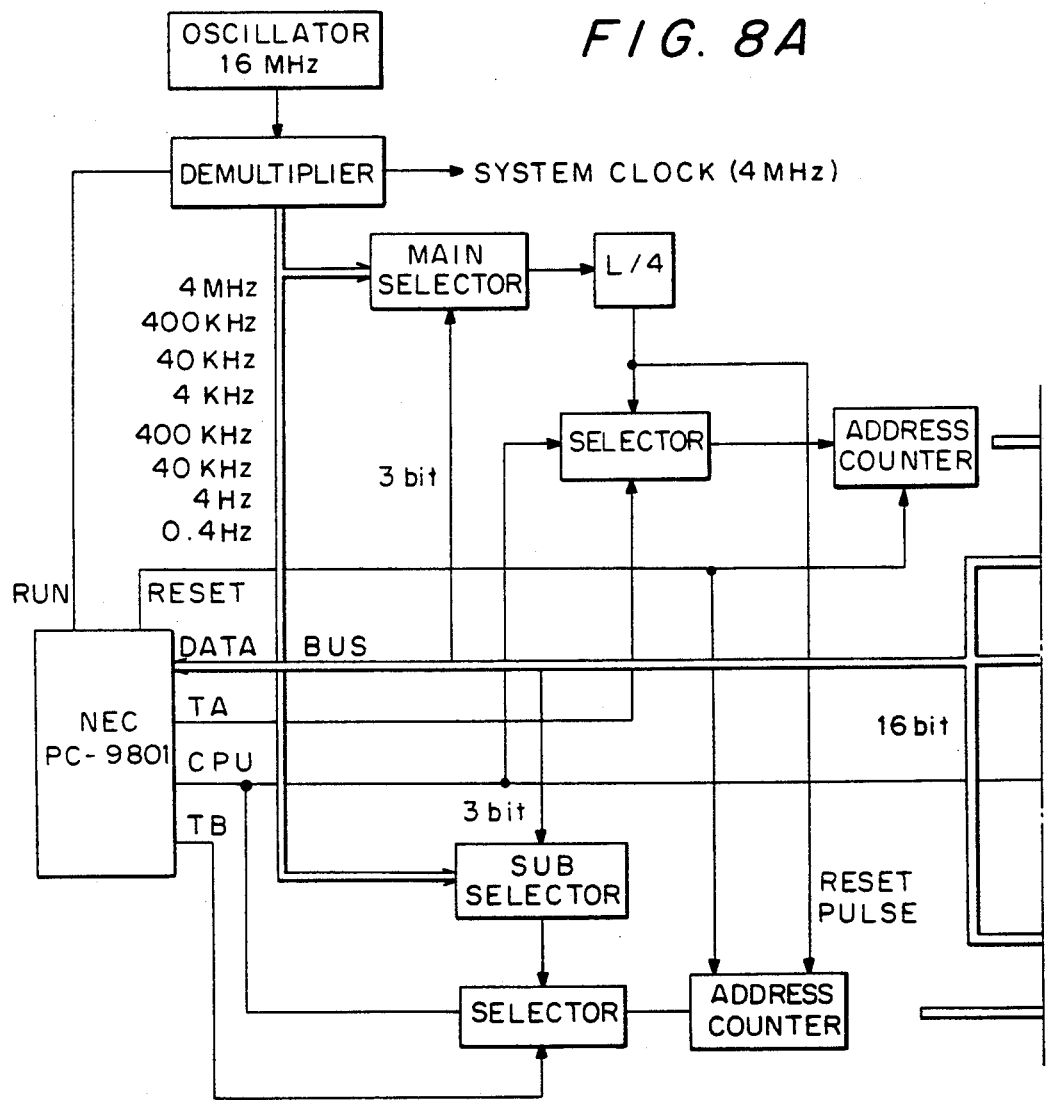
FIGS. 8(A and B) show a programmable stimulator for generating randomized double pulse electrical signals.
Figure 8B:
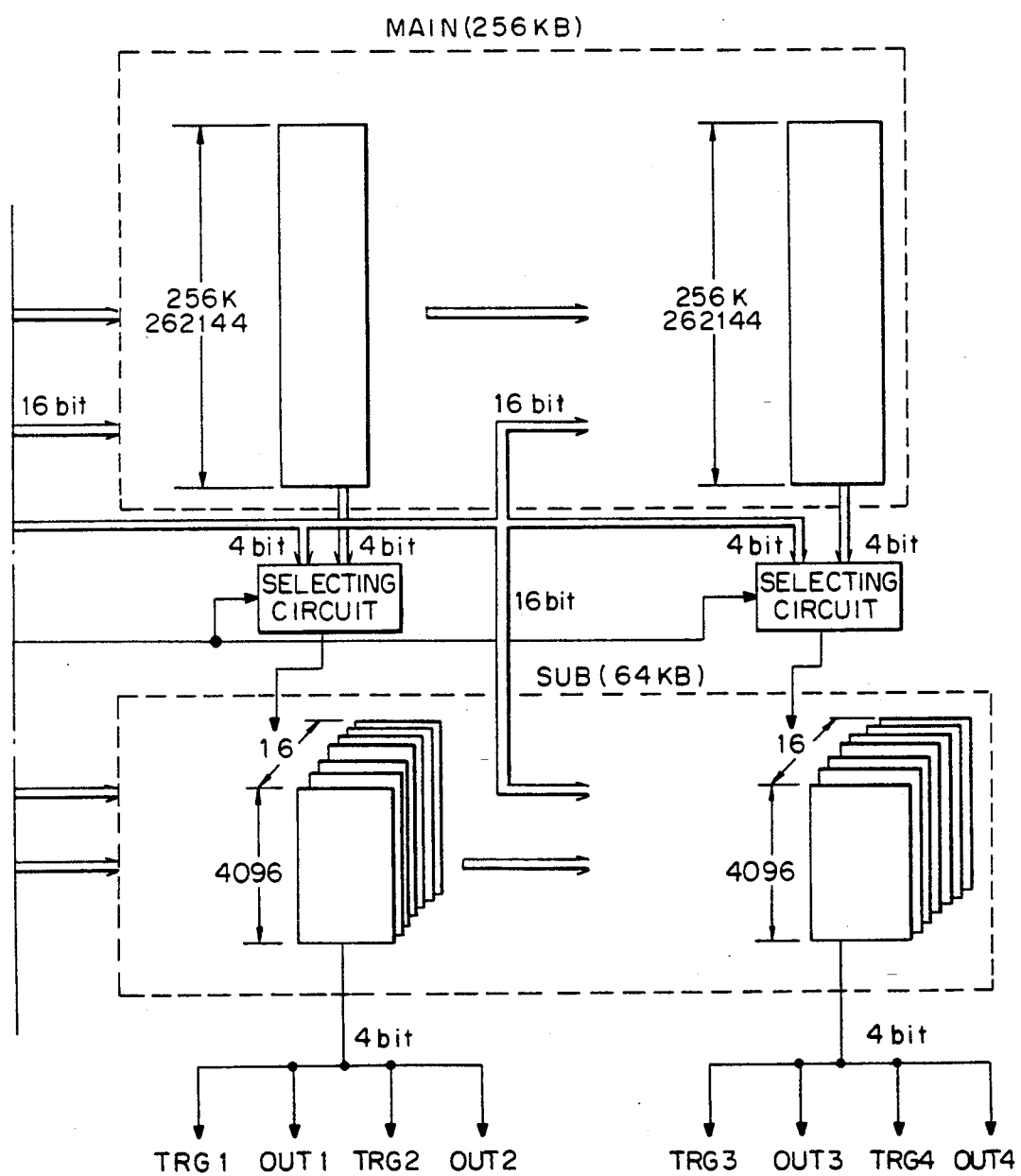

Stimulation and Recording Methods:

A programmable stimulator (see FIG. 8) was used to generate trains of double pulses at a constant baseline frequency of 5 Hz and randomly distributed interpulse intervals of 3, 4, 5, 8, 10, 20, 30, 50 and 80 msec. The first stimulus of each pair is called the "conditioning pulse" and the second stimulus called the "test pulse". A typical stimulation protocol used 2000 to 4000 pairs of pulses. A stimulator (WP Instruments, S8, New Haven, Conn.) and stimulus isolation units (WP Instruments, Model 305-I, New Haven, Conn.) were used to deliver the stimuli to the animal. FIG. 10A summarizes the RDP stimulation protocol. FIG. 10B also shows the actual number of double pulses delivered in for each interpulse interval when the stimulus trains consisted of 500-4000 double pulses. The programmable stimulator (FIG. 8) is constituted by a main-memory part and a sub-memory part. The former controls randomness, baseline frequencies, and repetition times of stimulation. The latter controls interpulse intervals. Using a host computer (NEC, 9801), stimulus patterns can be programmed in the memories of the main- and sub-memory parts.

To stimulate the spinal cord, the L5 dorsal root was cut 3 cm caudal to the dorsal root entry zone and draped on bipolar hook stimulating electrodes. Interelectrode distances were 5 mm and the cathode was placed proximal to the anode. Supramaximal stimulation was achieved with 0.1 msec pulses and twice the voltage required to elicit the largest compound action potential recorded from the dorsal root rostral to the stimulation site.

To record the responses evoked by the dorsal root stimulation, monopolar chlorided silver ball electrodes were placed on the dorsal midline of the spinal cord 10 mm rostral to the root entry zone. Dorsal root recordings were made at 10 mm caudal to the dorsal root entry zone (DREZ). In the experiments involving root compression, root responses were monitored 5 mm caudal to the root compression site as well. The reference electrode, also made of chlorided silver, was placed on paravertebral muscle adjacent to the laminectomy.

Figure 9:
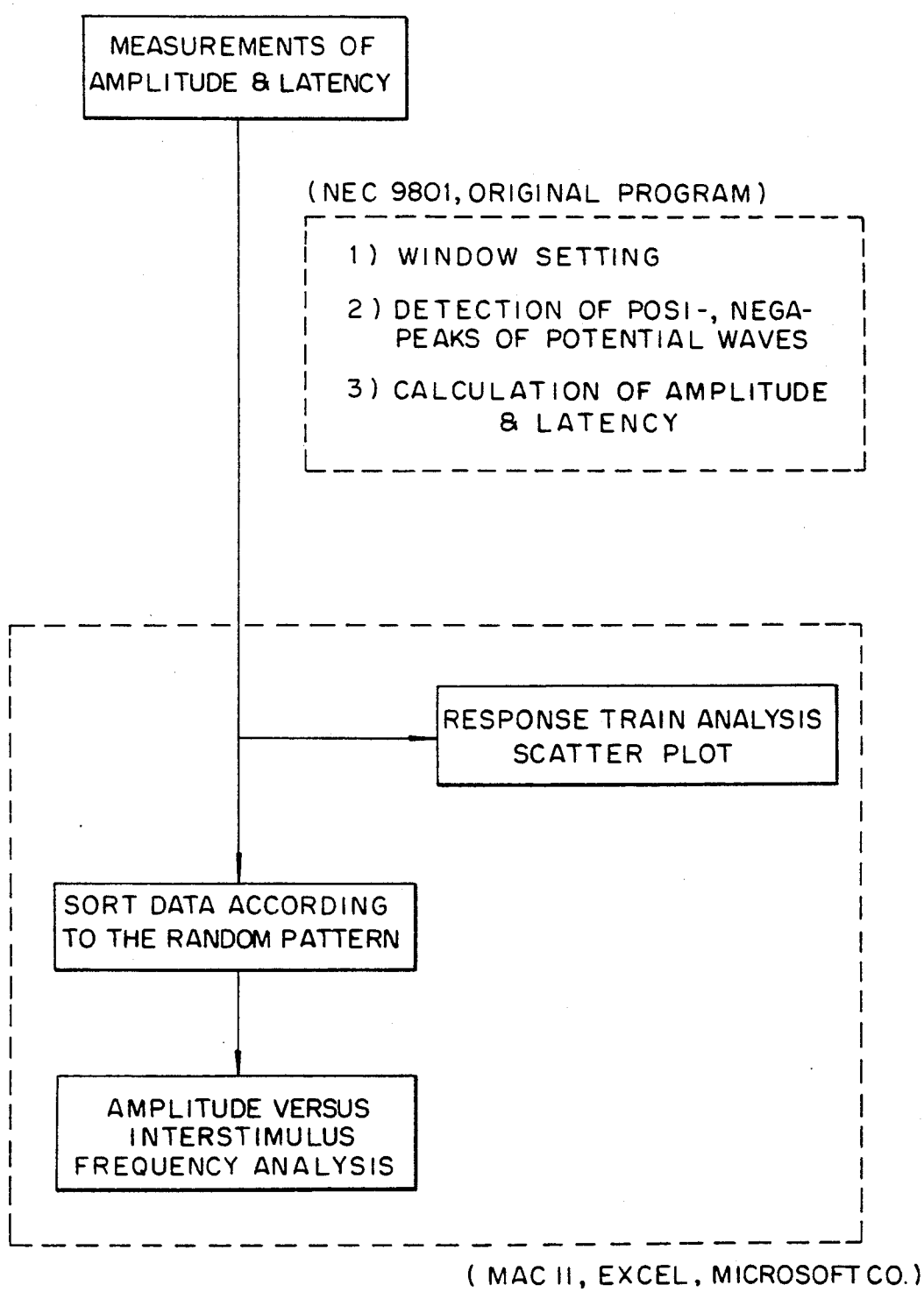
FIG. 9 shows a block diagram of software used for analysis of data in accordance with the invention.

The recorded responses were amplified with an AC preamplifier (A-M system, Model 1700, Everett, Wash.) with bandpass filters set at 0.08 and 5 KHz. The responses were displayed on an oscilloscope and digitally acquired with a microcomputer (NEC, 9801, Tokyo, Japan) with a 12 bit analog-to-digital conversion (Canopus, Model ADX-98, Kobe, Japan). Digital sampling was triggered 0.3 msec before each test pulse and sampled every 20-40 $\mu$sec. Response amplitudes and latencies were converted and sent by cable to a personal computer (Macintosh II, Apple Computer, Cupertino, Calif.) for analysis. A diagram of the data analysis block flow is shown in FIG. 9. Spinal Cord and Dorsal Root Injury:

The spinal cord, was compressed 5 mm from the L5 DREZ using a plastic plate (3×5 mm) with rounded edges. The plate was lowered with a micromanipulator (Narishige, Tokyo, Japan) in 0.25 mm increments until cord dorsum potentials activated by 1 Hz L5 root stimulation and recorded rostral to the compression site were completely abolished. The compression was then maintained at this level for 10 minutes and then released. In most cases, compression of the spinal cord by 2.0-2.5 mm produced conduction failure. The spinal compression was carried out in six rats.

To injure the L5 dorsal root, a pair of forceps was used to compress the root between the stimulation site and the dorsal root entry zone while monitoring the action potentials recorded at R1. Compression was repeated several times until the compound action potentials activated by 1 Hz stimulation and recorded rostral to the compression site decreased to half of pre-injury levels. This was carried out in four rats.

Action potential conduction in compressed spinal cords and dorsal roots recovered over 30-60 minutes after decompression After the action potentials in the dorsal column and dorsal root reached a stable phase an hour after decompression, the RDP stimulus protocol was begun. Experiments typically last 4-6 hours. When dorsal root response amplitudes fell more than 10% below pre-injury, the experiment was terminated.

Data Analysis:

Both the spinal and the root responses consisted of an initial triphasic spike (see FIGS. 11, 12) (positive($P_1$)-negative($N_1$)-positive($P_2$)). In FIGS. 11 and 12, negative is up, and positive is down, as shown. In the spinal cord, the spike is followed by a large negative and then a positive wave. These waves are smaller in the root response. Spinal response amplitudes were estimated from the initial positive peak to following negative peak of the triphasic spike ($P_1$, $N_1$, $P_2$). Response latency was measured from the stimulus artifact to the initial positive peak (FIG. 11B). Dorsal root response amplitudes were estimated from the peak-to-peak amplitude and onset latencies were estimated from the stimulus to the initial positivity of the triphasic spike.

Responses evoked by the test pulses were individually stored, sorted, and analyzed according to interpulse intervals. In order to correct for response fatigue during the train stimulation and deterioration of the preparation during the experiments, responses activated by the different interpulse intervals were compared against those activated by double pulses with 80 msec interpulse intervals. Responses activated by 80 msec double pulses were used as controls. Response amplitudes were expressed as percentage of control. Latencies were expressed in $\mu$sec difference from control.

Three analytical approaches were used to assess response changes due to spinal injury. First, amplitudes and latencies of responses were measured and averaged for each interpulse interval. Variances were indicated in standard deviations. Second, trends of response changes during the train stimulation were noted for each interpulse interval. Third, to assess changes in waveforms, responses from each interpulse interval were averaged. Response characteristics before and after injury were statistically compared by paired t-tests. Analysis of variance was used to assess the statistical significance of the differences for multiple time points. Differences due to injury were judged to be significant when the comparisons suggested probability values of <0.05.

Dorsal Column and Dorsal Root Responses Before Injury:

The dorsal column potentials evoked by L5 dorsal root stimulation in rats consisted of a triphasic spike (positive-negative-positive) and a large negative wave followed by a shallow positive wave (FIG. 11A). The initial positivity ($P_1$) of the triphasic spike can be clearly identified as the first peak of the response (FIG. 11B). The waveform of these spinal responses in rats closely resembles those observed in cats. The spinal triphasic spike has been attributed to the dorsal column compound action potential, reflecting activity in ascending collaterals of primary afferent fibers entering from the L5 dorsal root (Gasser et al, *Am. J. Physiol*, 103, 303-320 (1933)). The large negative wave is probably a synaptic potential.

Two characteristics of the triphasic spike in the spinal evoked potentials strongly suggest that the triphasic spike represents conducted dorsal column action potentials. First, in rats before injury, the onset latency of the spike was $0.62\pm0.1$ msec over a conduction distance of $34\pm2$ mm (n=6). This short conduction time virtually rules out synaptic transmission. The peak-to-peak amplitude of the spike was unaffected by stimuli frequencies of 300 Hz. Conduction involving synapses usually will not follow such high stimulation frequencies. Thus, in the following description and discussion of the data, the triphasic spike is the dorsal column compound action potential (CAP).

Dorsal root potentials recorded 10 mm caudal to the DREZ consisted of a triphasic spike followed by a small negative wave (FIGS. 11 and 12). The latency difference between the triphasic spike in the spinal cord and the dorsal root recordings suggest a conduction velocity of $48.6\pm2.9$ m/sec (mean$\pm$SD, n=6). The triphasic spike in the dorsal root potential will be called the dorsal root CAP in the following description.

Frequency Independent Spinal Conduction Changes After Injury:

Compression of the spinal cord by 2.0 to 2.5 mm abolished dorsal column CAP's activated by 1 Hz stimulation in the six rats studied. Although CAP recovery rates varied, all the rats recovered distinct action potentials within 30 minutes and the recovery stabilized after an hour. The responses usually did not recover fully and most rats showed 40-50% decreases in amplitude and 40-50% increases in latency.

Injury reduced the amplitudes and increased latencies of dorsal column CAP's activated by 1 Hz stimuli. FIG. 12A shows examples of dorsal column responses recorded from one rat before and three hours after injury. These waveforms were averaged (number=6). Before injury, the dorsal column CAP latency and amplitude were 0.54 msec and 1100 $\mu$V respectively. In this rat, 2.5 mm compression produced complete conduction block at 1 Hz. At three hours after injury, mean latency and amplitude of the CAP's were 0.76 msec and 650 $\mu$V.

The waveforms of dorsal column CAP's evoked by 1 Hz stimulation changed after spinal compression injury. Both the initial positivity ($P_1$) and the negativity ($N_1$) peaks had decreased slopes and the $N_1$ peak was broader (FIG. 12). The onset of $P_1$, not so distinct before injury, became even more difficult to identify. However, the $P_1$ peak generally remained clearly measurable. For that reason, it was elected to measure latencies from the stimulus to the peak of $P_1$ instead of using the $N_1$ peak or the onset of $P_1$. Likewise, the $P_1$ and $N_1$ peaks were sufficiently distinct to allow measurements of peak-to-peak amplitude differences.

Frequency Dependent Spinal Conduction Changes after Injury

Spinal cord compression altered the waveforms of dorsal column CAP's evoked by double pulses at different interpulse intervals. FIG. 12B shows the waveforms of dorsal column CAP's in a typical rat at 3 hours after compression. Compared to responses evoked by 80 msec double pulses, the waveform evoked by 3 msec double pulses showed rightward shifts of the $P_1$ peak and a decline of the $N_1$ peak. Comparisons of the N peak elicited at different interpulse intervals suggest the presence of a second $N_1$ component that was more affected by short interpulse intervals.

Injury selectively affected dorsal column conduction at short interpulse intervals frequencies. FIG. 13 summarizes the differences in amplitude and latency changes before and after compression injury in 6 rats. The ordinate indicates response amplitudes expressed as percentages of amplitude at 80 msec interpulse intervals (A), and response latency expressed in $\mu$sec difference from latency at 80 msec interpulse intervals (B). Abscissa indicates interpulse intervals in logarithmic scale. The error bars represent standard errors.

Before injury, response amplitudes and latencies did not change over the range of interpulse intervals tested except for slight amplitude augmentation at around 20 msec interpulse intervals. After injury, response amplitudes at interpulse intervals of 3, 4, and 5 msec were respectively $74.0\pm7.4\%$, $83.8\pm7.3\%$, and $93.0\pm5.7\%$ of control, significantly less than before injury ($p<0.01$). Likewise, response latencies at these interpulse intervals increased by $108\pm45$, $65\pm27$, and $39\pm17$ $\mu$sec respectively, significantly greater than before injury ($p<0.01$-$0.05$).

Before injury, dorsal column CAP's showed slightly increased response amplitudes at 20-50 msec interpulse intervals, compared with responses evoked at 80 msec intervals. This increase is small ($4.1\pm2.3\%$ at 20 msec interpulse interval) and significant ($p<0.01$). While all 6 rats studied showed significant amplitude decreases and latency increases at interpulse intervals of 3-5 msec, augmentation of the response at 20-50 msec interpulse intervals was not as consistent, occurring in only 4 of the 6 rats studied. Nevertheless, compression injury on average significantly increased this amplitude augmentation to $9.0\pm1.7\%$ ($p<0.02$) compared with preinjury responses.

Spinal Conduction Changes During Stimulation:

Compression injury increased the tendency of dorsal column CAP's to decline during RDP stimulation. Before injury, dorsal column CAP amplitudes showed only a slight or no tendency to change from the beginning to the end of a train of RDP stimulation. After injury, however, dorsal column CAP amplitudes gradually and significantly declined during RDP stimulation. An example is shown in FIG. 14A where dorsal column CAP's amplitudes for three interpulse intervals are plotted against the positions of the double pulses during the RDP stimulation. In FIG. 14A, the ordinate represents the CAP amplitude in $\mu$V and the abscissa indicates the number of test pulses of the RDP stimulation at each interpulse interval, that is, total number of the test pulses at a certain point is approximately equal to the number in abscissa multiplied by 9 (number of interpulse interval varieties). The amplitude at 80 msec is shown by open circles and the amplitude at 20 msec is shown by filled circles. The amplitude at 3 msec interpulse interval is shown by open triangles.

The declines in dorsal column CAP's during RDP stimulation were not the same for different interpulse intervals. Dorsal column CAP amplitudes associated with 3 msec interpulse intervals did not change during the stimulation even though the responses were much smaller than those evoked with 20 and 80 msec interpulse intervals. Response amplitudes at 20 msec interpulse intervals began decreasing shortly after onset of RDP and stabilized after the 50th stimulation. This trend was more prominent in the response amplitudes at 80 msec interpulse intervals.

To quantify the decline in response amplitudes during the train stimulation, the amplitudes of the first 20 (1st to 21st) responses were averaged and compared with the amplitudes of the last 20 (81st to 100th) responses of the stimulus trains. As shown in FIG. 14B, dorsal column CAP amplitudes of the first 20 did not differ significantly from the last 20 responses activated at interpulse intervals of 3-30 msec. However, differences were prominent at 50 and 80 msec interpulse intervals. FIG. 17 summarizes the statistical analyses of spinal evoked response amplitudes comparing the first 20 responses against subsequent groups of 20 responses, i.e. the second (21-40th), third (41-60th), fourth (61-80th), and fifth (81-100th) groups of 20 responses. The amplitude changes were small, on the order of 20-50 $\mu V$ compared to control amplitudes of 500-600 $\mu V$.

Dorsal Root Conduction Changes after Root Injury:

Dorsal root responses showed small changes between the beginning and the end of the experiments. Mean dorsal root CAP amplitudes at the end of the experiments were 90±0.8% of control (80 msec interpulse intervals) at 3 and 30 msec interpulse intervals. However, the dorsal root CAP's did not show conduction failure at 3-5 msec interpulse intervals. These findings suggest that the changes are not due to direct injury to the roots but may be changes relating to deterioration of the preparation. Such small changes in dorsal root CAP amplitudes at 3 msec interpulse intervals also do not explain the much larger changes in dorsal column CAP's after spinal injury.

The small changes in dorsal root responses prompted investigation of the effects of direct dorsal root compression to see if peripheral axons would show similar stimulus frequency dependent changes of conduction after injury as central axons. The L5 dorsal root was directly injured by pinching the root with forceps until the action potentials were reduced by about 50% in four rats. FIG. 15 shows an example of dorsal root CAP's recorded above the root compression site before and after the root pinch injuries. The waveforms represent averaged responses evoked by L5 dorsal root stimulation at 1Hz. The responses at different interpulse intervals are shown in FIG. 15A.

Compression injury of the L5 dorsal root produced stimulus frequency dependent conduction changes in the root. As summarized in FIG. 16, mean dorsal root CAP amplitudes declined precipitously at interpulse intervals of 3-10 msec. The pattern of the changes differ from spinal cord injury in several important respects. First, there was no tendency for amplitude augmentation at any interpulse interval. Second, the root injury did not increase the tendency of dorsal root CAP's to show fatigue during the stimulation, as shown in FIG. 16B. CAP amplitudes remained constant throughout the stimulation at all interpulse intervals tested. FIG. 16A shows averaged values of the first 100 responses at each interpulse interval, and normalized by those at 80 msec interpulse interval. The error bars represent standard deviations. There was no paradoxical augmentation in CAP amplitude at any interpulse interval. In FIG. 16B, the ordinate represents the CAV amplitude in $\mu V$ and the abscissa indicates the number of test pulses of the REDP stimulation at each interpulse interval.

Analysis of Test Results:

The randomized double pulse stimulation protocol revealed several phenomena in spinal cords and dorsal roots after compression injury. First, injured dorsal column axons showed significant compromises in conduction at 3-5 msec interpulse intervals. This conduction failure was not present before injury and suggests increased refractory periods of the injured axons surviving the compression injury. Second, analysis of response changes after injury revealed gradual declines in response amplitudes during the RDP stimulation, suggesting response fatigue. Third, injured spinal cords had augmented CAP amplitudes at 20-50 msec interpulse intervals compared with those at 80 msec interpulse intervals. Fourth, while injured dorsal root axons showed conduction failure at 3-10 msec interpulse intervals, they manifested neither the fatigue nor amplitude augmentation observed in the dorsal column CAP's after spinal cord compression. These findings will be discussed in sequence, followed by a summary of the strengths and pitfalls of RDP stimulation.

Conduction Failure at Short Interpulse Intervals:

Dorsal column and dorsal root CAP's conducting across the injury site showed significant amplitude decreases and latency increases at short interpulse intervals of 3-5 msec after injury In injured axons, conduction failure has been attributed to increased refractory periods. The data (FIG. 17) does not definitively demonstrate increased refractory periods because individual axonal activity was not recorded, but rather assessed extracellular field potentials representing populations of axons were used. This analysis cannot distinguish between decreased numbers of axons contributing to the CAP, increased temporal dispersion of action potentials, and non-specific declines in the amplitudes of action potentials. The last may be related to transient changes in extracellular volume, i.e., a decrease in tissue impedance which would decrease the field potentials generated by the same action currents.

Several observations, however, suggest that decreased CAP amplitudes and increased latencies at short interpulse intervals are due to alterations in axon populations contributing to the CAP rather than temporal dispersion. For example, the waveform changes of the responses are consistent with decreased axon numbers contributing to the CAP. The overall areas under the action potential decreased, as well as the peak amplitudes (see FIGS. 12B and 15B). Also, some components of the CAP seem to change more than others (FIG. 12B) which would not b consistent with volume changes which should affect the components non-selectively.

Spinal cord injury changes the axon population contributing to the CAP's Larger axons tend to be more sensitive to compression injury than smaller axons. Morphometric measurements have shown a clear propensity for selective loss of larger myelinated axons in the cat spinal contusion model. The surviving population of axons conducting after compression injury may be ones that normally have longer refractory periods. However, if a significant number of axons in the spinal cord have longer refractory periods, this population of axons would be expected to drop out at short interpulse intervals and consequently reduce CAP amplitude in uninjured spinal cords. This was not the case. Applicant's data suggests that the condition failure at short interpulse intervals is due to increased refractory periods in partly injured residual axons surviving the compression injury. This suggestion can be confirmed with single axon recordings in injured spinal cord during randomized double pulse stimulation.

Fatigue of Spinal Responses during RDP Stimulation:

Dorsal column CAP amplitudes decreased during RDP stimulation in injured spinal cords (FIG. 14A). At 5 Hz, a typical train of 2000 stimuli required 6-7 minutes to complete. Response amplitudes declined slowly and reached a plateau after several minutes of RDP stimulation. The progressive decline in response amplitudes was not uniform for different interpulse intervals and was most prominent at the longest interpulse interval tested, i.e., 80 msec. At short interpulse intervals of 3-5 msec, the response amplitudes did not change during the RDP stimulus train Dorsal root CAP's did not show any change during RDP stimulation and therefore cannot be responsible for this phenomenon.

The progressive decline of dorsal column CAP amplitude during the RDP stimulation represents fatigue of axonal conduction within the spinal cord. The mechanisms underlying this phenomenon may be distinct from those causing the conduction failure observed at small interpulse intervals. Many mechanisms may contribute to response fatigue during prolonged high frequency stimulation. For example, accumulations of intracellular sodium ions and extracellular potassium ions, loss of intracellular potassium ions, and other causes of axonal depolarization may lead to decreased action potential currents at the recording site. Other possibilities include progressive accommodation or increase in threshold of axons subjected to repeated stimulation and hence dropout of axons conducting across the lesion site.

Response fatigue was surprisingly most prominent at long interpulse intervals of 50-80 msec and absent at short interpulse periods of 3-5 msec. This finding may be explained in two ways. First, fatigue may develop only in injured axons that cannot transmit high frequency impulses, such as those evoked by double pulses with 3 msec interpulse intervals. At short interpulse intervals all these have failed to conduct, and therefore do not contribute to the CAP and hence no fatigue appears. Second, the causes of refractory periods may be similar to those causing fatigue and thus, at short interpulse intervals where refractory period mechanisms dominate, the mechanisms causing fatigue are already in play and therefore no longer can contribute to fatigue.

Augmentation of Spinal Responses After Injury:

Dorsal column CAP amplitudes increased at 20-50 msec interpulse intervals compared to 80 msec interpulse intervals. The timing of this response, i.e., following the refractory period, is reminiscent of the so-called supernormal period that sometimes occurs in demyelinated or unmyelinated axons. No change in response latency accompanied the increased amplitude in applicant's experiments (FIG. 13B). In the absence of latency shifts, any form of axonal hyperexcitability being the cause of the CAP amplitude increase is very unlikely.

Three other explanations of the CAP augmentation were rolled out. First, enlarged CAP's may represent axon recruitment at the stimulation site at certain interpulse intervals. However, this explanation is unlikely since dorsal root recordings showed no hint of CAP augmentation at any interpulse interval. Second, increased CAP amplitudes may result from better synchronization of action potentials. This explanation is also unlikely since there is no change in response latency associated with the increased amplitude. Third, changes in tissue impedance may increase field potential amplitudes. This possibility is unlikely because the changes in CAP amplitude occurred only at specific interpulse intervals.

The CAP augmentation may be an artifact of response fatigue. Response amplitudes are expressed as a percentage of response amplitudes at 80 msec intervals. Over the course of the stimulation, fatigue selectively reduces the amplitude of responses elicited by 80 msec double pulses. This will enhance the relative amplitude of responses activated with 3-50 msec double pulses. Due to the refractory period, response amplitudes will remain below 100% at short interpulse intervals of 3-10 msec. However, the intermediate interpulse of 20-50 msec will be artifactually increased. This explanation of the CAP augmentation is strongly supported by the absence of CAP augmentation in injured dorsal root responses that show no response fatigue during RDP stimulation.

Absence of Fatigue in Injured Dorsal Roots:

The dorsal roots did not exhibit response fatigue or amplitude augmentation at any interpulse interval tested before or after spinal cord compression injury. This finding gives added confidence that the dorsal column CAP changes observed are intrinsic to the spinal cord and not related to stimulus input changes during the experiments. Although injury to the roots resulted in conduction failure at short interpulse intervals of 3-10 msec, the dorsal root responses were remarkably stable after injury with no evidence of response fatigue or amplitude augmentation at any interpulse interval during the RDP train stimulation.

The lack of fatigue in injured dorsal roots is interesting because it suggests a difference between peripheral and spinal axonal responses to injury However, the compression injuries to the spinal cord and dorsal roots were qualitatively and quantitatively different. To injure the spinal cord, the spinal cord was progressing compressed until dorsal column conduction was abolished and then held the compression for 10 minutes. To injure the dorsal root, the nerve was pinched several times until root responses were reduced to half of pre-injury levels. The differences in injury method may account for the absence of fatigue in the injured dorsal roots. Repeated pinches of the dorsal roots with forceps may have produced all-or-none injuries of some dorsal root afferents while leaving surviving axons relatively intact.

The injured dorsal roots did show compound action potential condition failure across the injury site at interpulse intervals of 3-10 msec. Due to the short conduction distance in the dorsal roots, response latencies were not measured with sufficient accuracy (at 20 $\mu$sec sampling times) to show a latency shift due to the root injury. Nevertheless, applicant's data clearly shows that the surviving axons were unable to transmit high frequency impulses. This conduction failure was not present in normal dorsal roots and thus suggests that the axons remaining in the injured root were indeed damaged by the compression.

Advantages Provided by RDP Analysis

As can be seen from the above discussion of one possible domain of utility for the present invention, RDP evoked potentials provide three major advantages over conventional evoked potentials elicited with constant frequency stimulus trains First, within a single stimulus protocol, a wide range of stimulus frequencies can be investigated to quantify refractory periods, fatigue phenomenon, and any stimulus-frequency dependent excitability changes in injured axons. Second, because response amplitudes are expressed as a function of a stimulated response, a myriad of complicated factors influencing response amplitudes can be controlled. For example, surface recorded evoked potential amplitudes vary depending on electrode impedance and contact with the tissue. These sources of variability mitigate against comparisons of evoked potentials from experiment to experiment. In contrast, RDP evoked potentials will provide reproducible data concerning the refractory period, fatigue, and excitability changes despite these problems. Third, RDP activated evoked potentials are much more sensitive to injury than conventional evoked potentials. Our data shows remarkably small variances of response amplitudes. A power analysis based on the variances suggests that RDP evoked potentials can detect 1-2% changes in response amplitude at specific interpulse intervals.

One very attractive feature of RDP evoked potentials is that the protocol can be adapted to collect the same data obtained with conventional average evoked potentials. For example, one of the categories of interpulse intervals can be set at zero interpulse interval (i.e. a single pulse). The responses averaged from a zero impulse interval would be essentially equivalent to those collected by conventional evoked potentials. Because many responses can be acquired for each interpulse interval, RDP evoked potentials can be averaged and utilized in the same high noise environments as conventional averaged evoked potentials. Much of the information provided by RDP evoked potentials cannot be obtained via any other method.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for determining the behavior tendencies in response to repeated stimulation in a system in which a response evoked by such stimulation is measurable, comprising the steps of:
   (1) stimulating said system with a train of pairs of stimuli the first of each pair of stimuli in said train being the conditioning stimulus (CS) and the second of each said pair being the test stimulus (TS), wherein each said test stimulus is maintained at a constant intensity and said conditioning stimuli are applied at a constant frequency and wherein the interstimulus interval between each conditioning stimulus and its associated test stimulus, the conditioning stimulus intensity and/or the conditioning stimulus site is varied randomly between predetermined parameters;
   (2) measuring the response of said system evoked by said stimuli; and
   (3) analyzing the measured response to determine the behavioral tendencies.

2. A method in accordance with claim 1, wherein said system is a biological system.

3. A method in accordance with claim 2, wherein said biological system is selected from the group consisting of the neural, cardiovascular, skeletal muscle, visual, auditory, secretory, renal, hepatic, gastrointestinal, and genito-urinary systems.

4. A method in accordance with claim 2, wherein said stimuli are selected from the group consisting of electrical, electromagnetic, pharmacological, mechanical, thermal, hormonal, metabolic, or biochemical perturbations.

5. A method in accordance with claim 1, wherein said system is a non-biological system.

6. A method in accordance with claim 1, wherein in said stimulating step the intensity of said conditioning stimuli is varied and the site of the conditioning stimuli is maintained constant.

7. A method in accordance with claim 1, wherein the site of the conditioning stimuli is varied and the intensity of the conditioning stimuli is maintained constant.

8. A method in accordance with claim 1, wherein both the intensity and the site of the conditioning stimuli are varied randomly between predetermined parameters.

9. A method in accordance with claim 1, wherein the interstimulus interval between each conditioning stimulus and its associated test stimulus is varied and the conditioning stimulus intensity and the conditioning stimulus site is maintained constant.

10. A method in accordance with claim 1, wherein the interstimulus interval and the conditioning stimulus intensity are varied and the conditioning stimulus site is maintained constant.

11. A method in accordance with claim 2, wherein the evoked response for each conditioning stimulus is measured and the evoked response for each associated test stimulus is measured and the two values are compared to observe the recovery of the system.

12. A method in accordance with claim 1, wherein said measuring step comprises measuring both the amplitude and the latency of the response.

13. A method in accordance with claim 1, wherein said comparing step includes the step of plotting the average latency difference between the CS-evoked and TS-evoked responses against interstimulus frequency.

14. A method in accordance with claim 1, wherein said comparing step includes the step of plotting the latencies an amplitudes of individual TS-evoked and CS-evoked responses as a function of the stimulus pair number.

15. A method in accordance with claim 1, wherein the interstimulus interval and the conditioning stimulus intensity ar randomly varied and the conditioning stimulus site is maintained constant and wherein said analyzing step comprises separately averaging the percentage of the TS-evoked response to the corresponding CS-evoked response in each interstimulus interval and plotting said percentage as a function of interstimulus frequency.

16. A method in accordance with claim 2, wherein the interstimulus interval and the conditioning stimulus amplitude are varied and the conditioning stimulus site is maintained constant and wherein said analyzing step comprises determining the average latency difference between the TS-evoked and the corresponding CS-evoked response for each interstimulus interval and plotting the average latency difference against interstimulus frequency.

17. A method in accordance with claim 1, wherein the responses for each interstimulus interval, each CS-intensity category and each conditioning stimulus site are averaged or analyzed individually.

18. A method in accordance with claim 1, in which the amplitude or latency of each (nth) TS-evoked response is expressed as a percentage of the corresponding CS-evoked response and plotted against the amplitude or latency, respectively, of the next (n+1th) response.

19. A method for determining the behavior tendencies in a system undergoing repeated and varied perturbation, comprising the steps of:
measuring the intensity and time period from the immediately preceding perturbation (interperturbation interval) for each perturbation;
selecting each perturbation having an intensity which is substantially the same as a predetermined intensity; and
analyzing the intensity and interperturbation intervals of said selected perturbations to determine the behavior tendencies.

20. An apparatus for determing behavioral tendencies i response to repeated stimulation in a system in which a response evoked by such stimulation is measurable, comprising:
(1) generating means for generating a train of pairs of stimuli, the first of each pair of stimuli in said train being the conditioning stimulus (CS) and the second of each said pair being the test stimulus (TS), wherein each said test stimulus is maintained at a constant intensity and said conditioning stimuli are generated at a constant frequency and wherein the interstimulus interval between each conditioning stimulus and its associated test stimulus and/or the conditioning stimulus intensity is randomly varied between predetermined parameters;
(2) application means for applying said stimuli to the system being studied;
(3) detection means for detecting and measuring a response of said system to each said stimulus applied by said application means; and
(4) processing means for analyzing said measured responses to determine the behavior tendencies.

21. An apparatus in accordance with claim 20, wherein said detecting means detects and measures both the amplitude and latency of each said evoked response.

22. An apparatus in accordance with claim 20, wherein the system is a biological system and said stimuli are electrical stimuli.

23. An apparatus in accordance with claim 20, wherein said system is a biological system and said stimuli is electromagnetic radiation in the visual range and wherein said generating means varies the intensity and color of each said conditioning stimulus and also varies the interstimulus interval.

24. An apparatus in accordance with claim 20, wherein said stimuli are acoustic stimuli.

25. An apparatus in accordance with claim 20, and further including display means connected to said processing means for displaying the results of the analysis conducted by said processing means.

* * * * *

UNITED STATES PATENT AND TRADEMARK OFFICE
CERTIFICATE OF CORRECTION

PATENT NO. : 5,143,081
DATED : Sep. 1, 1992
INVENTOR(S) : Wise YOUNG and Kaoru SAKATANI It is certified that error appears in the above-identified patent and that said Letters Patent is hereby corrected as shown below:

```
Column 1, after the title, please insert
--This invention was funded by a research grant
from the National Institutes of Health, No. NS10164-21,
which provides the United States Government certain
rights in the invention.--
```

Signed and Sealed this

Twenty-eighth Day of December, 1993

Attest:

BRUCE LEHMAN

Attesting Officer

Commissioner of Patents and Trademarks